United States Patent
Greiveldinger-Poenaru et al.

(10) Patent No.: US 7,524,855 B2
(45) Date of Patent: Apr. 28, 2009

(54) SELECTED BENZOFURAN DERIVATIVES

(75) Inventors: Sorana Greiveldinger-Poenaru, Rheinfelden (CH); Khalid Islam, Reinach (CH); Dieter Gillessen, Pratteln (CH); Kaspar Burri, Binningen (CH)

(73) Assignee: Arpida AG (CH)

( * ) Notice: Subject to any disclaimer, the term of this patent is extended or adjusted under 35 U.S.C. 154(b) by 0 days.

(21) Appl. No.: 11/813,241

(22) PCT Filed: Dec. 13, 2005

(86) PCT No.: PCT/EP2005/013344

§ 371 (c)(1),
(2), (4) Date: Jul. 2, 2007

(87) PCT Pub. No.: WO2006/072370

PCT Pub. Date: Jul. 13, 2006

(65) Prior Publication Data

US 2008/0108610 A1    May 8, 2008

(30) Foreign Application Priority Data

Jan. 7, 2005    (WO) ................ PCT/EP2005/000072

(51) Int. Cl.
*C07D 405/06* (2006.01)
*C07D 405/14* (2006.01)
*A61K 31/505* (2006.01)

(52) U.S. Cl. ..................... 514/275; 544/324
(58) Field of Classification Search ................ 544/324; 514/275

See application file for complete search history.

(56) References Cited

FOREIGN PATENT DOCUMENTS

| EP | 0 096 214 A1 | 12/1983 |
| GB | 875562 | 8/1961 |
| WO | WO-02/10157 A1 | 2/2002 |
| WO | WO-2005/005418 A1 | 1/2005 |

OTHER PUBLICATIONS

Snyder et al., PubMed Abstract (J Med Liban. 48(4):208-14) Jul.-Aug. 2000.*

* cited by examiner

*Primary Examiner*—Deepak Rao
(74) *Attorney, Agent, or Firm*—Dickstein, Shapiro, LLP.

(57) ABSTRACT

The invention relates to new benzofuran derivatives and their use as active ingredients in the preparation of pharmaceutical compositions. The invention also concerns related aspects including processes for the preparation of the compounds, pharmaceutical compositions containing one or more of those compounds, and especially their use as anti-infectives.

13 Claims, No Drawings

SELECTED BENZOFURAN DERIVATIVES

The present invention relates to novel 2,4-diamino-5-(substituted) pyrimidines, to pharmaceutical compositions containing them, to processes for preparing them and their compositions, to intermediates for synthesising them and to their use in the treatment of microbial infections.

Certain 2,4-diamino-5-benzylpyrimidines have been demonstrated to be potent inhibitors of dihydrofolate reductase (DHFR), which catalyses the reduction of dihydrofolic acid to tetrahydrofolic acid (THFA). This property has been shown to result frequently in useful pharmaceutical properties particularly in the treatment of bacterial infections. Thus, U.K. Patent Specification No. 875,562 discloses inter alia 2,4-diamino-5-benzylpyrimidines wherein the benzyl moiety is substituted by three $C_{1-4}$ alkoxy groups.

Trimethoprim, 2,4-diamino-5-(3,4,5-trimethoxybenzyl) pyrimidine, is specifically disclosed in U.K. Patent No. 875, 562 and is the most active antibacterial agent amongst the 2,4-diamino-5-benzylpyrimidines known to date. Due to their mode of action, these benzylpyrimidines potentiate the antibacterial activity of the sulphonamides, and Trimethoprim has been used extensively over the last decade in human therapy in combination with various sulphonamides, and in particular with sulphamethoxazole, for the treatment of bacterial infections.

European Patent Applications Nos. 81109631.2 and 83104240.3 disclose inter alia also such types of compounds and their use.

In WO 02/10157 similar compounds are described. However, the compounds disclosed hereinafter exhibit a much more potent activity against DHFR including mutated enzyme, a superior bioavailability, and a superior antibacterial activity.

Thus, it has been found that a group of novel benzofuran derivatives are more potent than, e.g., Trimethoprim, and are active against Gram positive pathogens (*Staphylococcus aureus, Staphylococcus epidermidis, Enterococcus faecalis* or *Streptococcus pneumoniae*) and Gram negative pathogens (*Haemophilus influenzae, Escherichia coli, Klebsiella pneumoniae, Moraxella Cattharalis* or *Proteus vulgaris*). Furthermore, as mentioned above, the compounds of formula I show significantly improved activity against DHFR including mutated enzyme, a superior bioavailability, and a superior antibacterial activity.

Therefore, the present invention relates to novel compounds of the general formula I

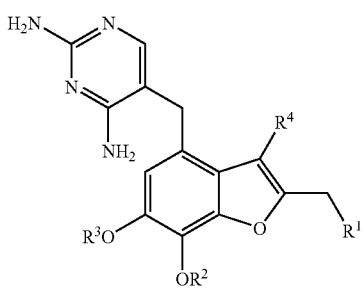

Formula I wherein
$R^1$ represents the groups

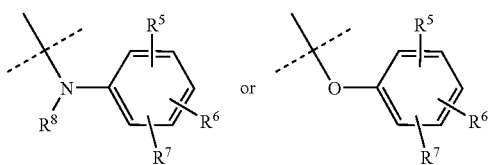

whereby in these groups $R^5$ is cyano, carboxylic acid or the group

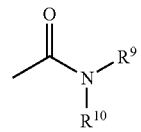

$R^9$ represents hydrogen, lower alkyloxy, lower alkylamino, lower alkyl with 1 to 6 carbon atoms, aminocarbonylalkyl, mono- or dialkylaminoalkyl, alkyloxyalkyl, arylalkyl, aryl, heteroaryl, whereby the aryl and heteroaryl group optionally are mono-, di- or tri- substituted with straight or branched chain lower alkyl with 1 to 4 carbon atoms, whereby these substituents may be the same or different;

$R^{10}$ represents hydrogen or lower alkyl with 1 to 4 carbon atoms;

$R^9$ and $R^{10}$ together with the nitrogen atom to which they are attached, form a 3-, 4-, 5- or 6- membered heterocyclic ring, whereby the 5- or 6- membered rings optionally contain an additional heteroatom which can be the same or different and are oxygen, nitrogen or sulfur, whereby the additional nitrogen can be substituted with lower alkyl with 1 to 4 carbon atoms, mono- or dialkylaminoalkyl or alkyloxyalkyl;

$R^6$ represents hydrogen, halogen, straight or branched chain lower alkyl with 1 to 4 carbon atoms, or lower alkyloxy;

$R^7$ represents hydrogen or halogen;

$R^8$ represents hydrogen or straight or branched chain lower alkyl with 1 to 4 carbon atoms;

$R^2$ and $R^3$ independently represent hydrogen; lower alkyl with 1 to 3 carbon atoms; or together a lower alkylene group with 1 to 3 carbon atoms bridging the oxygen atoms and forming a five, six or seven membered ring;

$R^4$ represents hydrogen or lower alkyl with 1 to 4 carbon atoms;

and pharmaceutically acceptable salts thereof.

In the definitions of the general formula I—if not otherwise stated—the expression lower alkyl means straight and branched alkyl chain groups with one to six carbon atoms, preferably 1 to 4 carbon atoms. Examples of lower alkyl and lower alkoxy groups with one to four carbon atom are methyl, ethyl, n-propyl, isopropyl, n-butyl, isobutyl, sec.-butyl, tert.-butyl, methoxy, ethoxy, propoxy, butoxy, iso-butoxy, sec.-butoxy and tert.-butoxy. The expression heteroaryl means six-membered aromatic rings containing one to four nitrogen atoms, benzo-fused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containing an oxygen and nitrogen atom and benzo-fused derivatives thereof, five-membered aromatic rings containing a sulfur and a nitrogen atom and benzo-fused derivatives thereof, five-membered aromatic rings containing two nitrogen atoms and benzo-fused derivatives thereof, five membered aromatic rings containing three nitrogen atoms and benzo-fused derivatives thereof or the tetrazolyl ring, e.g. furanyl, thienyl, pyrrolyl, pyridinyl, indolyl, quinolinyl, isoquinolinyl, imidazolyl, triazinyl, thiazinyl, thiazolyl, isothiazolyl, pyridazinyl, pyrazolyl, oxazolyl, isoxazolyl, etc. whereby such rings optionally are substituted with lower alkyl containing 1 to 4 carbon atoms. The expression aryl represents unsubstituted as well as mono-, di- or tri-substituted aromatic rings with 6 to 10 carbon atoms like phenyl or naphthyl rings, which optionally are substituted with C1-C4 lower alkyl. The expression heterocyclic ring represents saturated and unsaturated, but not aromatic, three-membered rings containing one hetero atoms, or four-, five- or six-membered rings containing one or two hetero atoms which may be the same or different and are nitrogen, oxygen or sulfur atoms. Examples are piperidinyl, morpholinyl, piperazinyl, pyrrolidinyl, dihydroimidazolyl, dihydropyrazoyl, pyrazolidinyl or dihydroxazolinyl, aziridine, azetidine. The expression halogen means fluorine, chlorine, bromine, and iodine but fluorine, chlorine and bromine are preferred.

One preferred group of compounds of the present invention are compounds of the general formula II Formula II wherein
$R^2$ and $R^3$ represent methyl;
$R^4$ represents hydrogen;
$R^5$, $R^6$, $R^7$ and $R^8$ are as defined in formula I.

A further preferred group of compounds of the present invention are compounds of the general formula III Formula III wherein
$R^2$ and $R^3$ represent methyl;
$R^4$ represents hydrogen and
$R^5$, $R^6$, $R^7$ and $R^8$ are as defined in formula I.

A further preferred group of compounds of the present invention are compounds of the general formula IV Formula IV wherein
$R^2$ and $R^3$ represent methyl;
$R^4$ represents hydrogen and
$R^5$, $R^6$, $R^7$ and $R^8$ are as defined in formula I;

A further preferred group of compounds of the present invention are compounds of the general formula V Formula V wherein
$R^2$ and $R^3$ represent methyl;
$R^4$ represents hydrogen and
$R^5$, $R^6$ and $R^7$ are as defined in formula I;

A further preferred group of compounds of the present invention are compounds of the general formula VI Formula VI wherein
$R^2$ and $R^3$ represent methyl;
$R^4$ represents hydrogen and $R^5$, $R^6$ and $R^7$ are as defined in formula I;

Preferred compounds are compounds of formula I, II, III, IV, V and VI wherein $R^5$ is carboxylic acid dimethylamide, carboxylic acid methylamide, carboxylic acid diethylamide, carboxylic acid methoxymethylamide, pyrrolidin-1-yl-methanone, morpholin-4-yl-methanone, carboxylic acid methylamide, piperidin-1-yl-methanone; carboxylic acid N-(1,3,5-trimethyl-1H-pyrazol-4-yl)-amide, carboxylic acid N-methyl-benzyl-amide, 4-(2-methoxy-ethyl)-piperazin1-yl-methanone, 4-(2-dimethylamino-ethyl)-piperazin1-yl-methanone, carboxylic acid N-(2-dimethylamino-ethyl)-N-methyl-amide, carboxylic acid N-butyl-N-methyl-amide, carboxylic acid N-isopropyl-N-methyl-amide, carboxylic acid N-carbamoylmethyl-N-methyl-amide , carboxylic acid or cyano;

$R^6$ represents hydrogen, fluoro, chloro or methoxy;

$R^7$ represents hydrogen, fluoro or chloro;

$R^8$ represents hydrogen or methyl.

Especially preferred compounds are compounds selected from the group consisting of:

(4-Chloro-2-{[4-(2,4-diamino-pyrimidin-5-ylmethyl)-6,7-dimethoxy-benzofuran-2-ylmethyl]-amino}-phenyl)-pyrrolidin-1-yl-methanone 4-Chloro-2-{[4-(2,4-diamino-pyrimidin-5-ylmethyl)-6,7-dimethoxy-benzofuran-2-ylmethyl]-amino}-N,N-diethyl-benzamide (4-Chloro-2-{[4-(2,4-diamino-pyrimidin-5-ylmethyl)-6,7-dimethoxy-benzofuran-2-ylmethyl]-amino}-phenyl)-piperidin-1-yl-methanone 4-Chloro-2-{[4-(2,4-diamino-pyrimidin-5-ylmethyl)-6,7-dimethoxy-benzofuran-2-ylmethyl]-amino}-N-(1,3,5-trimethyl-1H-pyrazol-4-yl)-benzamide N-Benzyl-4-chloro-2-{[4-(2,4-diamino-pyrimidin-5-ylmethyl)-6,7-dimethoxy-benzofuran-2-ylmethyl]-amino}-N-methyl-benzamide 4-Chloro-2-{[4-(2,4-diamino-pyrimidin-5-ylmethyl)-6,7-dimethoxy-benzofuran-2-ylmethyl]-amino}-N,N-dimethyl-benzamide 5-Chloro-2-{[4-(2,4-diamino-pyrimidin-5-ylmethyl)-6,7-dimethoxy-benzofuran-2-ylmethyl]-amino}-N,N-dimethyl-benzamide 4-Chloro-2-{[4-(2,4-diamino-pyrimidin-5-ylmethyl)-6,7-dimethoxy-benzofuran-2-ylmethyl]-methyl-amino}-N,N-dimethyl-benzamide 4-Chloro-2-{[4-(2,4-diamino-pyrimidin-5-ylmethyl)-6,7-dimethoxy-benzofuran-2-ylmethyl]-methyl-amino}-N-methyl-benzamide 2-{[4-(2,4-Diamino-pyrimidin-5-ylmethyl)-6,7-dimethoxy-benzofuran-2-ylmethyl]-methyl-amino}-4-fluoro-N,N-dimethyl-benzamide 2-{[4-(2,4-Diamino-pyrimidin-5-ylmethyl)-6,7-dimethoxy-benzofuran-2-ylmethyl]-amino}-5,N,N-trimethyl-benzamide 2-{[4-(2,4-Diamino-pyrimidin-5-ylmethyl)-6,7-dimethoxy-benzofuran-2-ylmethyl]-amino}-6-fluoro-N,N-dimethyl-benzamide 2-{[4-(2,4-Diamino-pyrimidin-5-ylmethyl)-6,7-dimethoxy-benzofuran-2-ylmethyl]-amino}-N,N-dimethyl-benzamide 2-{[4-(2,4-Diamino-pyrimidin-5-ylmethyl)-6,7-dimethoxy-benzofuran-2-ylmethyl]-amino}-4-fluoro-N,N-dimethyl-benzamide 3-Chloro-2-{[4-(2,4-diamino-pyrimidin-5-ylmethyl)-6,7-dimethoxy-benzofuran-2-ylmethyl]-amino}-N,N-dimethyl-benzamide 3,5-Dichloro-2-[4-(2,4-diamino-pyrimidin-5-ylmethyl)-6,7-dimethoxy-benzofuran-2-ylmethoxy]-N,N-dimethyl-benzamide 4-Chloro-2-[4-(2,4-diamino-pyrimidin-5-ylmethyl)-6,7-dimethoxy-benzofuran-2-ylmethoxy]-N-methyl-benzamide 2-[4-(2,4-Diamino-pyrimidin-5-ylmethyl)-6,7-dimethoxy-benzofuran-2-ylmethoxy]-5-fluoro-N,N-dimethyl-benzamide 2-{[4-(2,4-Diamino-pyrimidin-5-ylmethyl)-6,7-dimethoxy-benzofuran-2-ylmethyl]-amino}-3-methoxy-N,N-dimethyl-benzamide 2-{[4-(2,4-Diamino-pyrimidin-5-ylmethyl)-6,7-dimethoxy-benzofuran-2-ylmethyl]-methyl-amino}-N,N-dimethyl-benzamide 3,6-Dichloro-2-{[4-(2,4-diamino-pyrimidin-5-ylmethyl)-6,7-dimethoxy-benzofuran-2-ylmethyl]-amino}-N,N-dimethyl-benzamide 4-Chloro-2-[4-(2,4-diamino-pyrimidin-5-ylmethyl)-6,7-dimethoxy-benzofuran-2-ylmethoxy]-N,N-dimethyl-benzamide (4-Chloro-2-{[4-(2,4-diamino-pyrimidin-5-ylmethyl)-6,7-dimethoxy-benzofuran-2-ylmethyl]-amino}-phenyl)-morpholin-4-yl-methanone 4-Chloro-2-{[4-(2,4-diamino-pyrimidin-5-ylmethyl)-6,7-dimethoxy-benzofuran-2-ylmethyl]-amino}-benzonitrile 4-Chloro-2-{[4-(2,4-diamino-pyrimidin-5-ylmethyl)-6,7-dimethoxy-benzofuran-2-ylmethyl]-amino}-N-isopropyl-N-methyl-benzamide N-Butyl-4-chloro-2-{[4-(2,4-diamino-pyrimidin-5-ylmethyl)-6,7-dimethoxy-benzofuran-2-ylmethyl]-amino}-N-methyl-benzamide 4-Chloro-2-{[4-(2,4-diamino-pyrimidin-5-ylmethyl)-6,7-dimethoxy-benzofuran-2-ylmethyl]-amino}-benzoic acid 4-Chloro-2-{[4-(2,4-diamino-pyrimidin-5-ylmethyl)-6,7-dimethoxy-benzofuran-2-ylmethyl]-amino}-N-(2-dimethylamino-ethyl)-N-ethyl-benzamide (4-Chloro-2-{[4-(2,4-diamino-pyrimidin-5-ylmethyl)-6,7-dimethoxy-benzofuran-2-ylmethyl]-amino}-phenyl)-[4-(2-dimethylamino-ethyl)-piperazin-1-yl]-methanone (4-Chloro-2-{[4-(2,4-diamino-pyrimidin-5-ylmethyl)-6,7-dimethoxy-benzofuran-2-ylmethyl]-amino}-phenyl)-[4-(2-methoxy-ethyl)-piperazin-1-yl]-methanone N-Carbamoylmethyl-4-chloro-2-{[4-(2,4-diamino-pyrimidin-5-ylmethyl)-6,7-dimethoxy-benzofuran-2-ylmethyl]-amino}-N-methyl-benzamide and pharmaceutically acceptable salts thereof.

The invention also relates to a process for the manufacture of compounds of the general formula I

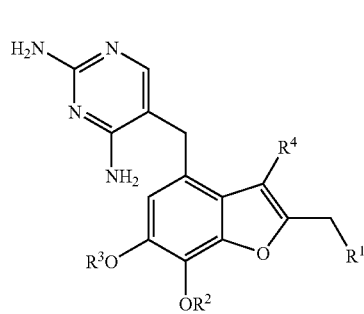

Formula I wherein
R¹ represents the groups

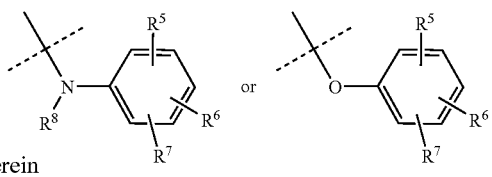

wherein
$R^2$, $R^3$, $R^4$, $R^5$, $R^6$, $R^7$, and $R^8$ have the meaning given in formula I above which process comprises reacting—as depicted in Scheme 1—a compound of the general formula VII (see PCT Publication WO 02/10157), with the anhydride VIII, wherein $R^{11}$ represents straight or branched chain lower alkyl to give the fully protected compound IX. The allyl group of the compound IX is then cleaved using tetrakis(triphenylphosphine)palladium as catalyst, to give the compound of general formula X.

Scheme 1

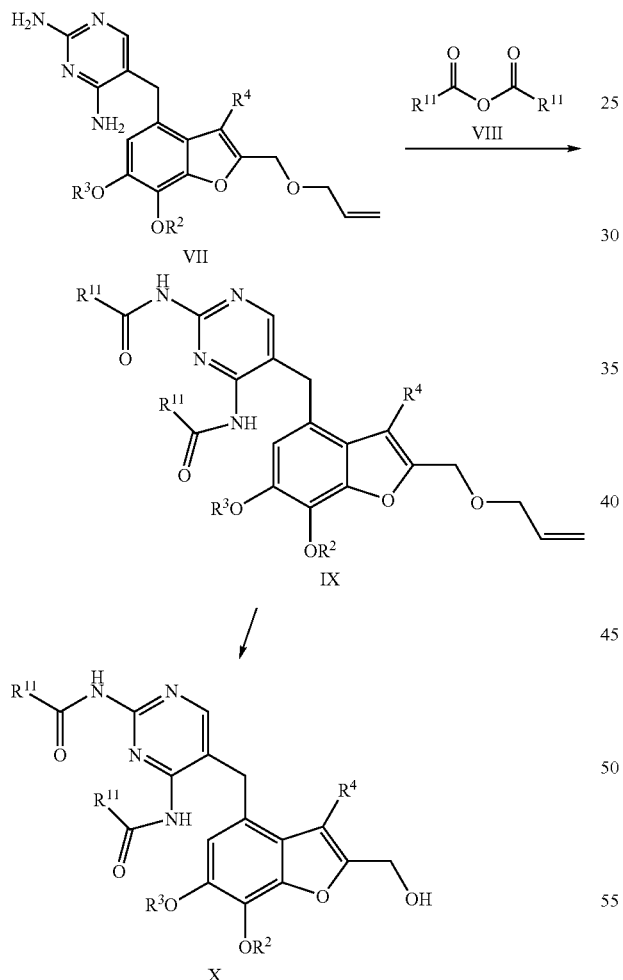

The intermediates of the general formula X are novel compounds which serve as intermediates in the synthesis of active compounds of general formula I. The intermediate X (Scheme 2) can be coupled with the corresponding anthranilic acid derivatives XI under acidic conditions, such as p-toluenesulfonic acid, to give to the compound of general formula XII, wherein R¹ is defined as in formula I. Treatment of the compound XII with an excess of aqueous sodium hydroxide solution gives the desired compound of general formula I.

Scheme 2

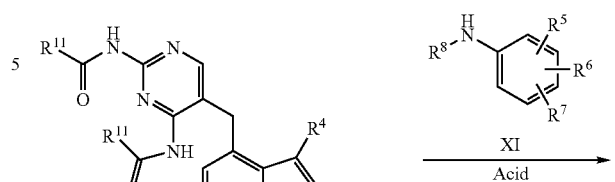

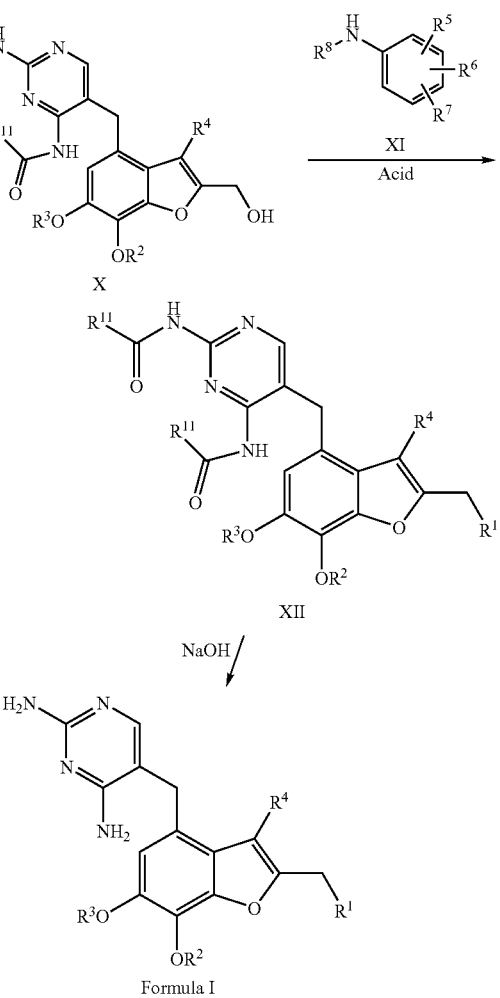

Some of the unknown anthranilic acid derivatives of general formula XI,

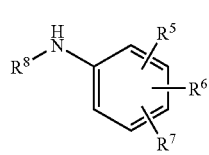

wherein $R^5$ represents the group

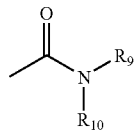

and $R^6$, $R^7$, $R^8$, $R^9$ and $R^{10}$ have the meaning given in formula I above, are synthesised by reacting the anthranilic acids XIII, (which, when $R^8$ represents lower alkyl, can be obtained by the reductive amination reaction with the corresponding aldehyde according to General Procedure C (compare experimental part)), with the amine XIV using standard peptide coupling reagents such as N-Ethyl-N'(3-dimethylaminopropyl)carbodiimide hydrochloric acid salt (EDC) and 1-Hydroxybenzotrialzole (HOBT) or O-(benzotriazol-1-yl)-

N,N,N',N'-tetramethyluronium tetrafluoroborate (TBTU) as described in Scheme 3. The anthranilic acid derivatives XI thus obtained are coupled with the compounds X, using the same procedure as described above in Scheme 2, to give the compound of general formula I.

The intermediates of the general formula XVI are novel compound which serve as intermediates in the synthesis of active compounds of general formula I.

The alcohol X was activated by reacting it with sulfonyl chloride compounds of formula XV, wherein $R^{12}$ represents lower alkyl or aryl, to give the intermediate XVI. The compound XVI thus obtained was reacted with the anthranilic acid derivatives XI, using Lewis acids such as $ZnCl_2$, to give the compound XII. Further treatment with aqueous base gave the compound of general formula I as described in Scheme 4.

Access to an alternative array of substituents can also be achieved by following the synthetic Scheme 5.

The intermediates of the general XVII are novel compounds, which serve as intermediates in the synthesis of active compounds of general formula I.

The alcohol X was oxidized using an excess of manganese dioxide to give the aldehyde XVII. The compound XVII thus obtained was reacted with the anthanilic acid derivative XI, using reductive amination conditions. The Schiff base was formed under acidic conditions, or adding triethylorthoformate as dehydrating agent and it was then reduced with sodium borohydride to give the compound of formula XII.

Final treatment with base gave the compound of general formula I as described in Scheme 5.

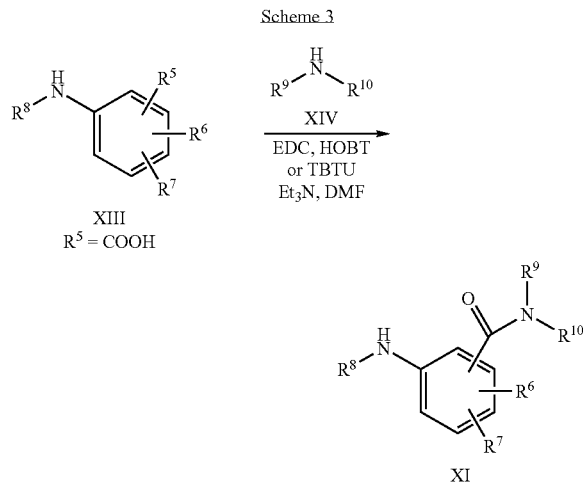

Access to an alternative array of substituents can be achieved by proceeding according to Scheme 4.

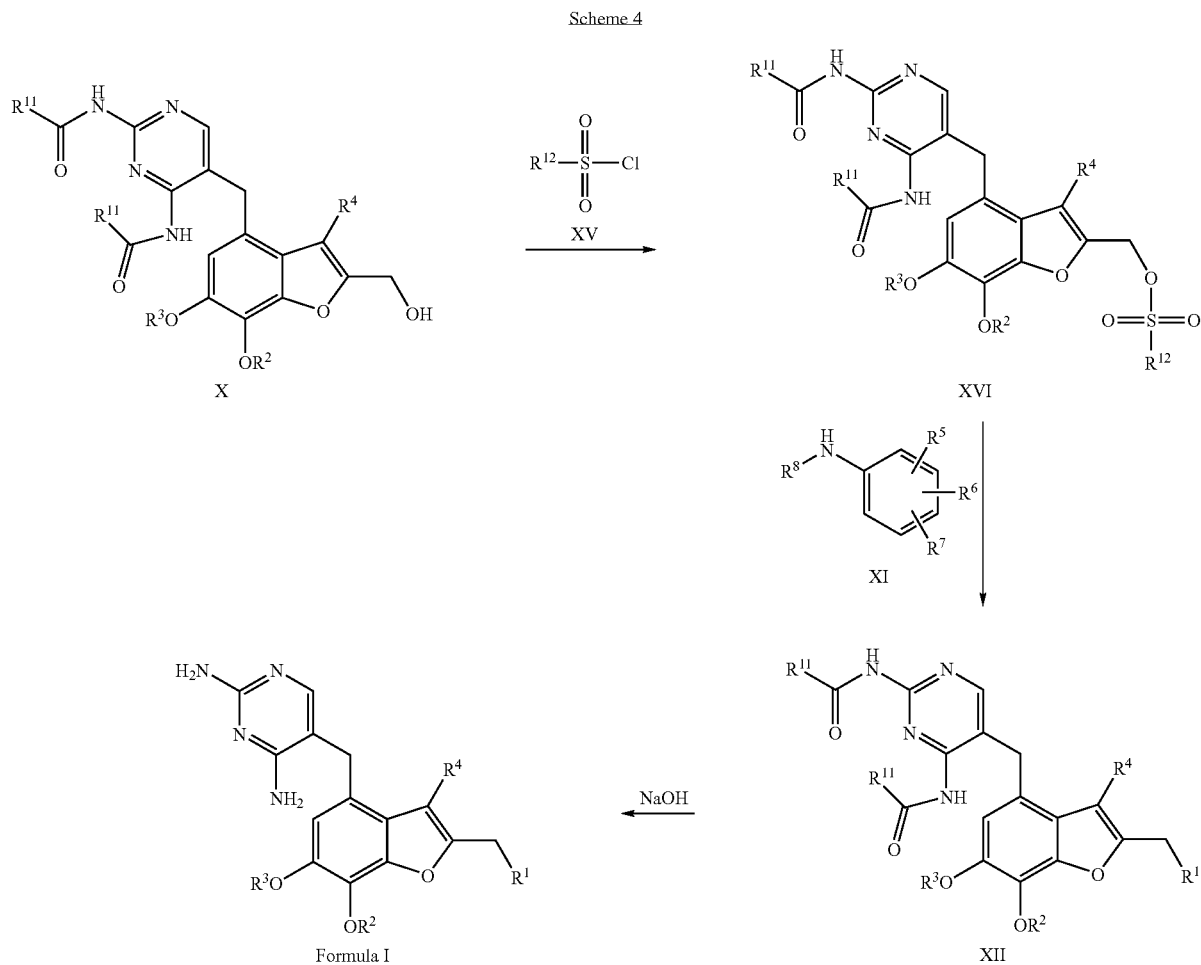

Scheme 5

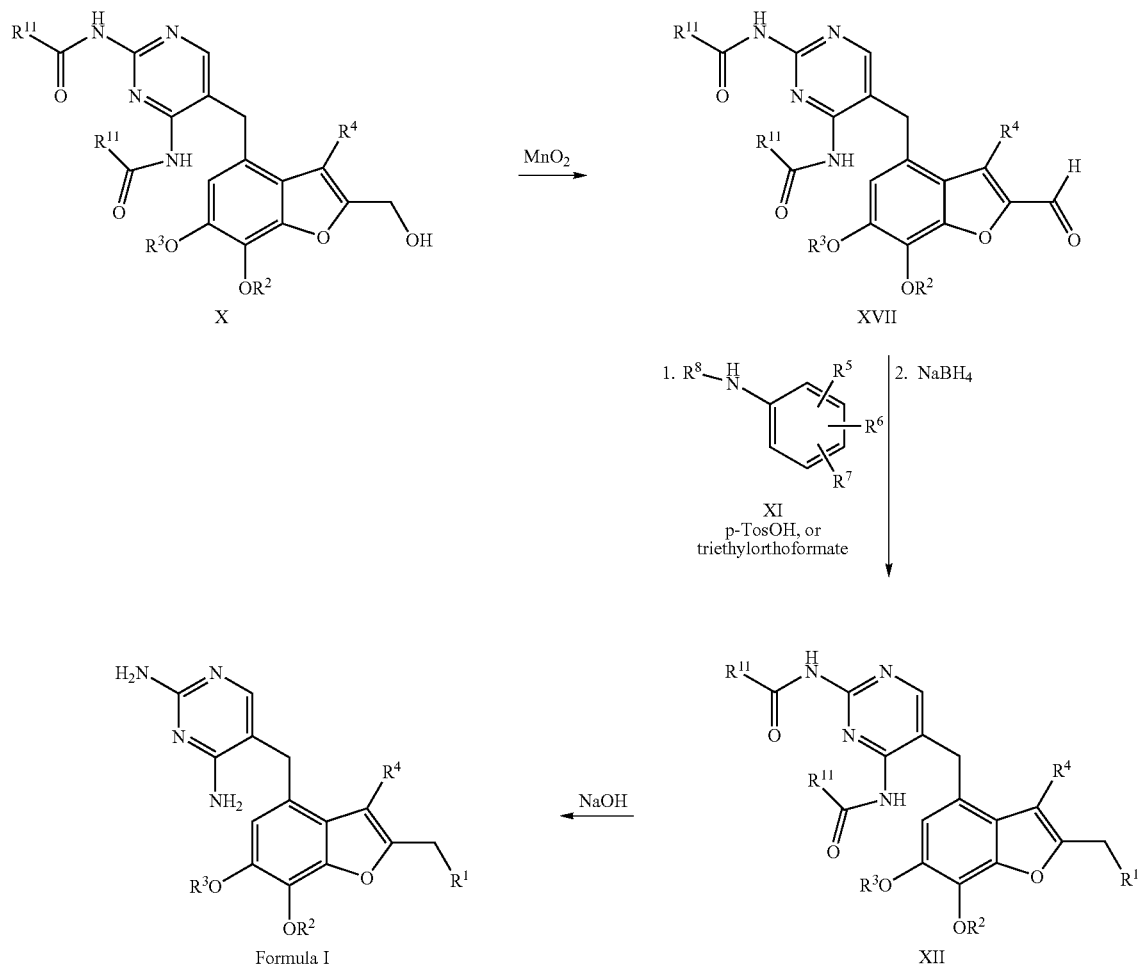

An alternative procedure can be used to synthesise the compounds of general formula I. The compound XVII was reacted with the aniline XVIII, wherein $R^5$ is define as in formula I, using reductive amination conditions. The Schiff base was formed under strong acidic conditions, such as trifluoroacetic acid, and it was then reduced with sodium borohydridetriacetoxy to give the mixture XIX as describe in Scheme 6. In the specific case of $R^5$ being carboxylic acid, a further coupling with the corresponding amines XIV using standard amide coupling procedures with O-(benzotriazol-1-yl)-N,N,N',N'-tetramethyluronium tetrafluoroborate (TBTU) as coupling reagent was performed. Final treatment with base gave the compound of general formula I as described in Scheme 6.

Scheme 6

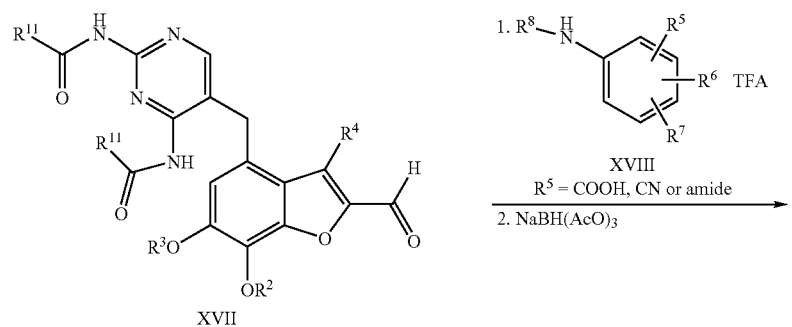

-continued

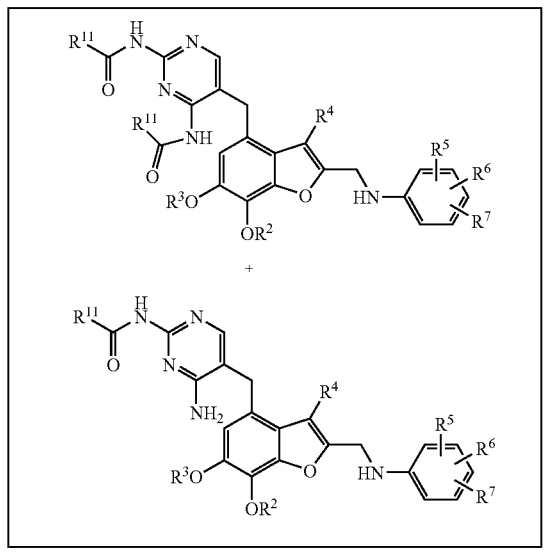

Mixture XIX 1. amine XIV, TBTU;
2. NaOH
If $R^5$ = COOH to follow 1 and 2
If $R^5$ = COOH, CN or amide to follow 2

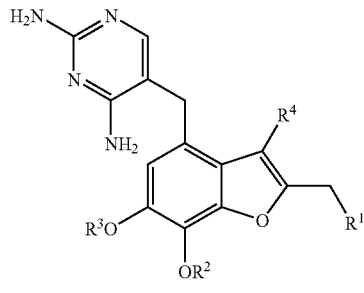

Formula I

The invention also relates to a process for the manufacture of compounds of the general formula I

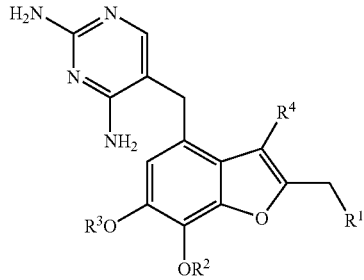

Formula I wherein
$R^1$ represents the groups

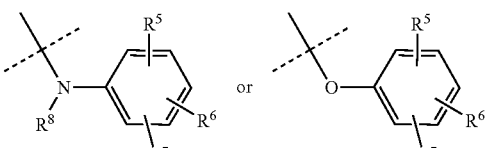

and $R^2$, $R^3$, $R^4$, $R^5$, $R^6$, $R^7$ and $R^8$ have the meaning given in formula I above, which process comprises reacting under basic conditions—as depicted in Scheme 7—a compound of the general formula XX (see PCT Publication WO 02/10157), with the corresponding anthranilic acid derivatives or phenol XXI, wherein Z represents, $NHR^8$ or OH.

Scheme 7

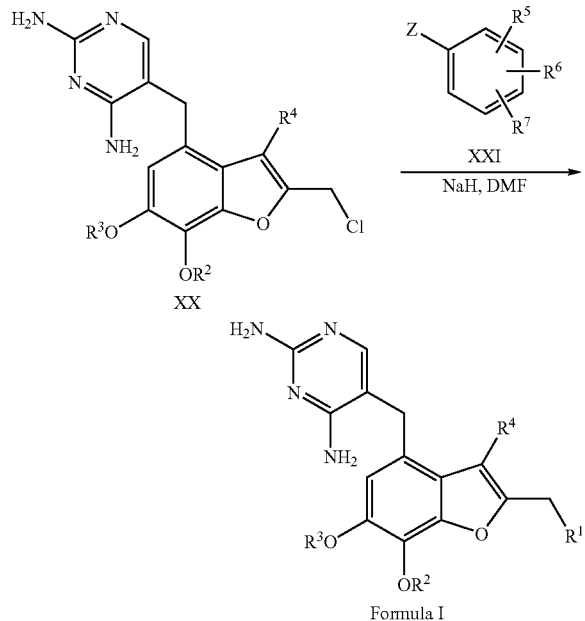

Formula I

Experimental Part

Abbreviations:
ACN: Acetonitrile
ATCC: American type culture collection
$CH_2Cl_2$: Dichloromethane
DMF: Dimethyl formamide
DMSO: Dimethyl sulfoxide
EDC: N-Ethyl-N'(3-dimethylaminipropyl)carbodiimide hydrochloric acid salt
eq.: equivalent
ESI: Electrospray ionisation
EtOH: Ethanol
FC: Flash chromatography
HOBT: 1-hydroxybenzotriazole
HPLC: High performance liquid chromatography
$KHSO_4$: Potassium hydrogen sulfate
MeOH: Methanol
$MgSO_4$: Magnesium sulfate
MS: Mass spectrometry
NMR: Nuclear magnetic resonance
p-TosOH: p-toluenesulfonic acid
TFA: Trifluoroacetic acid
THF: Tetrahydrofuran
TLC: Thin layer chromatography
TBTU: O-(benzotriazol-1-yl)-N,N,N',N'-tetramethyluronium tetrafluoroborate General Procedure A: Protection of Diaminopyrimidine Group (Scheme 1)

Under argon and at room temperature, compound VII (1 eq.) was suspended in the anhydride VIII (2.5 eq.). The suspension was stirred and heated at 150° C. until of a clear solution was obtained. After completion of the reaction (6 hours), ethyl acetate was added and the organic layer was washed with water, a saturated solution of $NaHCO_3$, brine and dried over $MgSO_4$. After evaporation of the solvent under reduced pressure, compound IX was obtained and used without further purification.

EXAMPLE 1

Following General Procedure A, N-[5-(2-allyloxymethyl-6,7-dimethoxy-benzofuran-4-ylmethyl)-4-(2,2-dimethyl-propionylamino)-pyrimidin-2-yl]-2,2-dimethyl-propionamide (quantitative yield from HPLC-MS profile) was obtained as a brown oil by reacting (5-(2-allyloxymethyl-6,7-dimethoxy-benzofuran-4-ylmethyl)-pyrimidine-2,4-diamine) (1 eq., 5 g, 13.5 mmol) and pivalic acid anhydride (2.5 eq., 7.0 mL, 34.5 mmol).

MS ESI: 539.2 $[M+H]^+$

General Procedure B: Cleavage of Allyl (Scheme 1)

Under argon, to a solution of compound IX (1 eq.) in ACN was added tetrakis-(triphenylphosphin)-palladium (0.25 eq.) and ammonium formate (5 eq.). The resulting mixture was heated at 80° C. until completion of the reaction. The mixture was quenched with water, and extracted with ethyl acetate. The organic layer was washed with water, brine, dried over $MgSO_4$, and evaporated under reduced pressure. The compound X was obtained after purification by FC (cyclohexane: EtOAc).

EXAMPLE 2

Following General Procedure B, N-[4-(2,2-dimethyl-propionylamino)-5-(2-hydroxymethyl-6,7-dimethoxy-benzofuran-4-ylmethyl)-pyrimidin-2-yl]-2,2-dimethyl-propionamide (quantitative yield from HPLC-MS profile) was obtained by reacting N-[5-(2-allyloxymethyl-6,7-dimethoxy-benzofuran-4-ylmethyl)-4-(2,2-dimethyl-propionyl-amino)-pyrimidin-2-yl]-2,2-dimethyl-propionamide (5 g, 9.29 mmol, 1 eq.), tetrakis-(triphenylphosphin)-palladium (2.68 g, 2.32 mmol, 0.25 eq.) and ammonium formate (2.93 g, 46.46 mmol, 5 eq.).

MS ESI: 499.2 $[M+H]^+$.

EXAMPLE 3

Following General Procedure A with isobutyric anhydride to obtain N-[5-(2-allyloxymethyl-6,7-dimethoxy-benzofuran-4-ylmethyl)-2-isobutyrylamino-pyrimidin-4-yl]-isobutyramide and following General procedure B for the cleavage of the allyl group, N-[5-(2-hydroxymethyl-6,7-dimethoxy-benzofuran-4-ylmethyl)-2-isobutyrylamino-pyrimidin-4-yl]-isobutyramide was obtained and used for the next step without further purification.

MS ESI: 471.0 $[M+H]^+$

General Procedure C: Methylation of Anthranilic Acid Derivatives

Under argon and at room temperature, to a solution of anthranilic acid derivative XI wherein $R^8$ is hydrogen (1 eq.) in ACN sodium cyanoborohydride (3.5 eq.) and formaldehyde (1.3 eq.) were added. After 5 minutes of stirring, the pH of the reaction mixture was ajusted to pH 3 with a 1N HCl solution. After completion of the reaction, the mixture was diluted with dichloromethane, and the organic layer was washed with a saturated solution of $NaHCO_3$ and brine. After drying over $MgSO_4$ and evaporating under reduced pressure, the compound XI wherein $R^8$ is methyl was obtained and used without further purification.

EXAMPLE 4

Following General Procedure C, 4-fluoro-2-methylamino-benzoic acid (830 mg, 76%) was obtained by reacting 2-amino-4-fluoro-benzoic acid (1 g, 6.44 mmol), sodium cyanoborohydride (1.62 g, 25.76 mmol), and formaldehyde (667 μL, 8.37 mmol).

MS ESI: 170.1 [M+H]$^+$

EXAMPLE 5

Following General Procedure C, 4-chloro-2-methylamino-benzoic acid (1.61 g, 75%) was obtained by reacting 4-chloro-2-amino-benzoic acid (2 g, 11.66 mmol), sodium cyanoborohydride (2.93 g, 46.64 mmol), and formaldehyde (1.21 mL, 15.16 mmol).

MS ESI: 186.0 [M+H]$^+$

General Procedure D: Amide Formation (Scheme 3)

Under argon and at room temperature, to a solution of compound XIII (1 eq.) in DMF, was added amine XIV (1 to 5 eq.). 1-Hydroxybenzotriazole hydrate (1.2 eq.), (3-dimethylamino-propyl)-ethyl-carbodiimide hydrochloride (1.2 eq.) and, if needed, triethylamine (1 to 3 eq.) were then added. After completion of the reaction, the reaction mixture was diluted with ethyl acetate, and the organic layer was then washed with a 0.1M solution of KHSO$_4$, a saturated solution of NaHCO$_3$, water, and brine. After drying over MgSO$_4$ and evaporating under reduced pressure, the compound XI was obtained and used without further purification.

EXAMPLE 6

Following General Procedure D, (2-amino-4-chloro-phenyl)-pyrrolidin-1-yl-methanone (1.37 g, 99%) was obtained by reacting 2-amino-4-chloro-benzoic acid (1 g, 5.82 mmol), pyrrolidine (578 μL, 6.99 mmol), 1-hydroxybenzotriazole hydrate (945 mg, 6.99 mmol), and (3-dimethylamino-propyl)-ethyl-carbodiimide hydrochloride (1.34 g, 6.99 mmol).

MS ESI: 225 [M+H]$^+$

EXAMPLE 7

Following General Procedure D, 2-amino-4-chloro-N,N-diethyl-benzamide (1.25 g, 95%) was obtained by reacting 2-amino-4-chloro-benzoic acid (1 g, 5.82 mmol), diethylamine (369 μL, 6.99 mmol), 1-hydroxybenzotriazole hydrate (945 mg, 6.99 mmol), and (3-dimethylamino-propyl)-ethyl-carbodiimide hydrochloride (1.34 g, 6.99 mmol).

MS ESI: 227 [M+H]$^+$

EXAMPLE 8

Following General Procedure D, 2-amino-4-chloro-N-(1,3,5-trimethyl-1H-pyrazol-4-yl)-benzamide (164 mg, 72%) was obtained by reacting 2-amino-4-chloro-benzoic acid (140 mg, 0.79 mmol), 1,3,5-trimethyl-1H-pyrazol-4-ylamine (500 mg, 3.99 mmol), 1-hydroxybenzotriazole hydrate (130 mg, 0.96 mmol), (3-dimethylamino-propyl)-ethyl-carbodiimide hydrochloride (183 mg, 0.96 mmol), and triethylamine (220 μL, 1.60 mmol).

MS ESI: 279 [M+H]$^+$

EXAMPLE 9

Following General Procedure D, 2-amino-4-fluoro-N,N-dimethyl-benzamide (quantitative yield from HPLC-MS profile) was obtained by reacting 2-amino-4-fluoro-benzoic acid (1 g, 6.44 mmol), dimethylamine hydrochloride (630 mg, 7.73 mmol), 1-hydroxybenzotriazole hydrate (1.04 g, 7.73 mmol), (3-dimethylamino-propyl)-ethyl-carbodiimide hydrochloride (1.48 g, 7.73 mmol), and triethylamine (2.68 mL, 19.3 mmol).

MS ESI: 183.1 [M+H]$^+$

EXAMPLE 10

Following General Procedure D, 2-amino-4-chloro-N,N-dimethyl-benzamide (10.36 g, 89%) was obtained by reacting 2-amino-4-chloro-benzoic acid (10 g, 58.3 mmol), dimethylamine hydrochloride (5.71 g, 70.0 mmol), 1-hydroxybenzotriazole hydrate (9.45 g, 70.0 mmol), (3-dimethylamino-propyl)-ethyl-carbodiimide hydrochloride (13.41 g, 70.0 mmol), and triethylamine (24.3 mL, 70.0 mmol).

MS ESI: 199.0 [M+H]$^+$

EXAMPLE 11

Following General Procedure D, 2-amino-6-fluoro-N,N-dimethyl-benzamide (1.78 g, 76%) was obtained by reacting 2-amino-6-fluoro-benzoic acid (2 g, 12.9 mmol), dimethylamine hydrochloride (1.26 g, 15.9 mmol), 1-hydroxybenzotriazole hydrate (2.09 g, 15.5 mmol), (3-dimethylamino-propyl)-ethyl-carbodiimide hydrochloride (2.97 g, 15.5 mmol), and triethylamine (9.4 mL, 38.7 mmol).

MS ESI: 183.1 [M+H]$^+$

EXAMPLE 12

Following General Procedure D, 4-fluoro-N,N-dimethyl-2-methylamino-benzamide (quantitative yield from HPLC-MS profile) was obtained by reacting 4-fluoro-2-methylamino-benzoic acid (410 mg, 2.43 mmol), dimethylamine hydrochloride (238 mg, 2.92 mmol), 1-hydroxybenzotriazole hydrate (395 mg, 2.92 mmol), (3-dimethylamino-propyl)-ethyl-carbodiimide hydrochloride (560 mg, 2.92 mmol), and triethylamine (1.01 mL, 7.29 mmol).

MS ESI: 197.0 [M+H]$^+$

EXAMPLE 13

Following General Procedure D, 5-chloro-N,N-dimethyl-2-methylamino-benzamide (610 mg, 71%) was obtained by reacting 5-chloro-2-methylamino-benzoic acid (750 mg, 4.05 mmol), dimethylamine hydrochloride (396 mg, 4.86 mmol), 1-hydroxybenzotriazole hydrate (656 mg, 4.86 mmol), (3-dimethylamino-propyl)-ethyl-carbodiimide hydrochloride (931 mg, 4.86 mmol) and triethylamine (1.7 mL, 12.15 mmol).

MS ESI: 213.0 [M+H]$^+$

EXAMPLE 14

Following General Procedure D, 4-chloro-N,N-dimethyl-2-methylamino-benzamide (859 mg, 99%) was obtained by reacting 4-chloro-2-methylamino-benzoic acid (750 mg, 4.05 mmol), dimethylamine hydrochloride (396 mg, 4.86 mmol), 1-hydroxybenzotriazole hydrate (656 mg, 4.86 mmol), (3-dimethylamino-propyl)-ethyl-carbodiimide hydrochloride (931 mg, 4.86 mmol), and triethylamine (1.7 mL, 12.15 mmol).

MS ESI: 213.0 [M+H]$^+$

EXAMPLE 15

Following General Procedure D, 2-chloro-N,N-dimethyl-6-methylamino-benzamide (309 mg, 43%) was obtained by reacting 2-chloro-6-methylamino-benzoic acid (630 mg, 3.41 mmol), dimethylamine hydrochloride (334 mg, 4.09 mmol), 1-hydroxybenzotriazole hydrate (552 mg, 4.09 mmol), (3-dimethylamino-propyl)-ethyl-carbodiimide hydrochloride (781 mg, 4.09 mmol) and triethylamine (1.12 mL, 10.23 mmol).

MS ESI: 213.0 [M+H]+

EXAMPLE 16

Following General Procedure D, 2-amino-3-chloro-N,N-dimethyl-benzamide (750 mg, 65%) was obtained by reacting 2-amino-3-chloro-benzoic acid (1 g, 5.83 mmol), dimethylamine hydrochloride (571 mg, 7.00 mmol), 1-hydroxybenzotriazole hydrate (945 mg, 7.00 mmol), (3-dimethylamino-propyl)-ethyl-carbodiimide hydrochloride (1.34 g, 7.00 mmol) and triethylamine (2.43 mL, 17.49 mmol).

MS ESI: 199.0 [M+H]+

EXAMPLE 17

Following general procedure D, 4-chloro-2-hydroxy-N,N-dimethyl-benzamide (1.82 g, 78%) was obtained by reacting 4-chloro-2-hydroxy-benzoic acid (2 g, 11.60 mmol), dimethylamine hydrochloride (1.14 g, 13.92 mmol), 1-hydroxybenzotriazole hydrate (1.87 g, 13.92 mmol), (3-dimethylamino-propyl)-ethyl-carbodiimide hydrochloride (2.66 g, 13.92 mmol) and triethylamine (4.84 mL, 34.80 mmol).

MS ESI: 200.1 (M+H)

EXAMPLE 18

Following General Procedure D, 5-fluoro-2-hydroxy-N,N-dimethyl-benzamide (1.02 g, 43%) was obtained by reacting 5-fluoro-2-hydroxy-benzoic acid (2 g, 12.8 mmol), dimethylamine hydrochloride (1.25 g, 15.36 mmol), 1-hydroxybenzotriazole hydrate (2.07 g, 15.36 mmol), (3-dimethylamino-propyl)-ethyl-carbodiimide hydrochloride (2.94 g, 15.36 mmol) and triethylamine (4.88 mL, 38.78 mmol).

MS ESI: 184.0 [M+H]+

EXAMPLE 19

Following General Procedure D, (2-amino-4-chloro-phenyl)-morpholin-4-yl-methanone (quantitative yield from HPLC-MS profile) was obtained by reacting 2-amino-4-chloro-benzoic acid (100 mg, 0.58 mmol), morpholine (61 µL, 0.70 mmol), 1-hydroxybenzotriazole hydrate (95 mg, 0.70 mmol), (3-dimethylamino-propyl)-ethyl-carbodiimide hydrochloride (134 mg, 0.70 mmol) and triethylamine (161 µL, 1.16 mmol).

MS ESI: 241.1 [M+H]+

General Procedure E: Amide Formation with TBTU

Under argon and at room temperature, to a solution of anthranilic acid XIII (1 eq.) in DMF, were added sequentially amine XIV (5 eq.), O-(benzotriazol-1-yl)-N,N,N',N'-tetramethyluronium tetrafluoroborate (1 to 5 eq.) and, if needed, triethylamine (2 eq.). After completion of the reaction, the mixture was diluted with ethyl acetate and the organic layer was washed with a saturated solution of NaHCO₃, water and brine. The resulting organic phase was dried over MgSO₄ and evaporated under reduced pressure to give the corresponding amide XI, which was used without further purification.

EXAMPLE 20

Following General Procedure E, 2-amino-N-benzyl-4-chloro-N-methyl-benzamide (1.52 g, 95%) was obtained by reacting 2-amino-4-chloro-benzoic acid (1 g, 5.83 mmol), benzyl-methyl-amine (3.75 mL, 29.1 mmol), O-(benzotriazol-1-yl)-N,N,N',N'-tetramethyluronium tetrafluoroborate (2.2 g, 6.86 mmol).

MS ESI: 275.1 [M+H]+

EXAMPLE 21

Following General Procedure E, 2-amino-N-carbamoylmethyl-4-chloro-N-methyl-benzamide (545 mg, 77%) was obtained by reacting 2-amino-4-chloro-benzoic acid (500 mg, 2.91 mmol), 2-methylamino-acetamide hydrochloride (362 mg, 2.91 mmol), O-(benzotriazol-1-yl)-N,N,N',N'-tetramethyluronium tetrafluoroborate (1.86 g, 5.82 mmol) and triethylamine (810 µL, 5.82 mmol).

MS ESI: 241.9 [M+H]+

EXAMPLE 22

Following General Procedure E, 2-amino-4-chloro-N-isopropyl-N-methyl-benzamide (quantitative yield from HPLC-MS profile) was obtained by reacting 2-amino-3,5-dichlorobenzoic acid (10 g, 58.41 mmol), isopropyl-methyl-amine (30 mL, 292.0 mmol), O-(benzotriazol-1-yl)-N,N,N',N'-tetramethyluronium tetrafluoroborate (22.5 g, 70.09 mmol).

MS ESI: 227.1 [M+H]+

General Procedure F: Coupling Procedure Using p-toluenesulfonic Acid (Scheme 2)

Under argon and at room temperature, to a solution of X (1 to 1.2 eq.) in acetonitrile, p-toluenesulfonic acid (2.5 eq.) and the anthranilic acid derivative XI (1 eq.) were added. The reaction mixture was stirred and heated at 70° C. until completion of the reaction. The reaction mixture was quenched with a saturated solution of NaHCO₃ and extracted with dichloromethane. The organic layer was washed with water, a saturated solution of NaCl, dried over MgSO₄ and evaporated under reduced pressure. The compound XII (1 eq.) so obtained was dissolved in methanol or isopropanol and an excess of a 4N NaOH solution (10 eq.) was added. The resulting mixture was heated at 50° C. until completion. The reaction was quenched with water, and extracted with dichloromethane. The organic layer was washed with a saturated solution of NaHCO₃, water, and brine, and it was dried over MgSO₄ and evaporated under reduced pressure. The compound I was obtained after purification by FC, eluting with a gradient from CH₂Cl₂ to CH₂Cl2/methanol (9/1).

EXAMPLE 23

Following General Procedure F, (4-chloro-2-{[4-(2,4-diamino-pyrimidin-5-ylmethyl)-6,7-dimethoxy-benzofuran-2-ylmethyl]-amino}-phenyl)-pyrrolidin-1-yl-methanone (41 mg, 19%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (200 mg, 0.40 mmol), p-toluenesulfonic acid (159 mg, 0.83 mmol), (2-amino-4-chloro-phenyl)-pyrrolidin-1-yl-methanone (75 mg, 0.33 mmol), and 4N NaOH (293 µL, 1.17 mmol).

MS ESI: 539.0 [M+H]+

EXAMPLE 24

Following General Procedure F, 4-chloro-2-{[4-(2,4-diamino-pyrimidin-5-ylmethyl)-6,7-dimethoxy-benzofuran-2-ylmethyl]-amino}-N,N-diethyl-benzamide (45 mg, 21%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (200 mg, 0.40 mmol), p-toluenesulfonic acid (159 mg, 0.83 mmol) 2-amino-4-chloro-N,N-diethyl-benzamide (76 mg, 0.33 mmol), and 4N NaOH (335 µL, 1.34 mmol).

MS ESI: 537.0 [M+H]$^+$

EXAMPLE 25

Following General Procedure F, (4-chloro-2-{[4-(2,4-diamino-pyrimidin-5-ylmethyl)-6,7-dimethoxy-benzofuran-2-ylmethyl]-amino}-phenyl)-piperidin-1-yl-methanone (38 mg, 17%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (200 mg, 0.40 mmol), p-toluenesulfonic acid (159 mg, 0.83 mmol), (2-amino-4-chloro-phenyl)-piperidin-1-yl-methanone (80 mg, 0.33 mmol), and 4N NaOH (267 µL, 1.06 mmol).

MS ESI: 551.0 [M+H]$^+$

EXAMPLE 26

Following General Procedure F, 4-chloro-2-{[4-(2,4-diamino-pyrimidin-5-ylmethyl)-6,7-dimethoxy-benzofuran-2-ylmethyl]-amino}-N-(1,3,5-trimethyl-1H-pyrazol-4-yl)-benzamide (17 mg, 7%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (200 mg, 0.40 mmol), p-toluenesulfonic acid (191 mg, 1.00 mmol) and 2-amino-4-chloro-N-(1,3,5-trimethyl-1H-pyrazol-4-yl)-benzamide (113 mg, 0.40 mmol) and 4N NaOH (524 µL, 2.09 mmol).

MS ESI: 590.9 [M+H]$^+$

EXAMPLE 27

Following General Procedure F, N-benzyl-4-chloro-2-{[4-(2,4-diamino-pyrimidin-5-ylmethyl)-6,7-dimethoxy-benzofuran-2-ylmethyl]-amino}-N-methyl-benzamide (60 mg, 25%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (200 mg, 0.40 mmol), p-toluenesulfonic acid (191 mg, 1.00 mmol), 2-amino-N-benzyl-4-chloro-N-methyl-benzamide (150 mg, 0.40 mmol), and 4N NaOH (757 µL, 3.03 mmol).

MS ESI: 586.9 [M+H]$^+$

General Procedure G: Coupling with Anthranilic Acid Derivatives and Zinc Chloride (Scheme 4)

Under argon, and at 0° C., to a solution of X (1 eq.) in dichloromethane, sulfonyl chloride XV, e.g. methanesulfonyl chloride (1.2 eq.) and triethylamine (1.2 eq.) were added. The resulting mixture was stirred at room temperature until completion. After quenching the reaction with water, the layers were separated. The organic phase containing the compound XVI was then dried over MgSO$_4$, and used for next synthetic step.

Under argon and at room temperature, to a solution of the anthranilic acid derivative XI (1.2 eq.) in dichloroethane, zinc chloride (1 to 1.2 eq.) was added. After stirring for 10 minutes, the previously obtained solution of XVI (1 eq.) in dichloromethane was added. After completion of the reaction, the mixture was quenched with a saturated NaHCO$_3$ solution and extracted with dichloromethane. The organic layer was washed with water, brine, dried over MgSO$_4$ and evaporated under reduced pressure to give compound XII, which was used without further purification.

The compound XII (1 eq.) so obtained was dissolved in methanol or isopropanol and an excess of a 4N NaOH solution (10 eq.) was added. The resulting mixture was heated at 50° C. until completion. The reaction was quenched with water, and extracted with dichloromethane. The organic layer was washed with a saturated solution of NaHCO$_3$, water, brine, dried over MgSO$_4$ and evaporated under reduced pressure. The compound I was obtained after purification by FC, eluting with a gradient from CH$_2$Cl$_2$ to CH$_2$Cl$_2$/methanol (9/1).

EXAMPLE 28

Following General Procedure G, 4-chloro-2-{[4-(2,4-diamino-pyrimidin-5-ylmethyl)-6,7-dimethoxy-benzofuran-2-ylmethyl]-amino}-N,N-dimethyl-benzamide (2 g, 76%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (2.57 g, 5.15 mmol), methanesulfonyl chloride (480 µL, 6.18 mmol), triethylamine (861 µL, 6.18 mmol), zinc chloride (840 mg, 6.18 mmol), 2-amino-4-chloro-N,N-dimethyl-benzamide (1.23 g, 6.18 mmol), and 4N NaOH (2.42 mL, 9.68 mmol).

MS ESI: 511.2 [M+H]$^+$

EXAMPLE 29

Following General Procedure G, 5-chloro-2-{[4-(2,4-diamino-pyrimidin-5-ylmethyl)-6,7-dimethoxy-benzofuran-2-ylmethyl]-amino}-N,N-dimethyl-benzamide (77 mg, 25%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (300 mg, 0.60 mmol), methanesulfonyl chloride (60 µL, 0.72 mmol), triethylamine (100 µL, 0.72 mmol), zinc chloride (83 mg, 0.61 mmol), 2-amino-5-chloro-N,N-dimethyl-benzamide (121 mg, 0.61 mmol), and 4N NaOH (309 µL, 1.23 mmol).

MS ESI: 511.0 [M+H]$^+$

EXAMPLE 30

Following General Procedure G, 4-chloro-2-{[4-(2,4-diamino-pyrimidin-5-ylmethyl)-6,7-dimethoxy-benzofuran-2-ylmethyl]-methyl-amino}-N,N-dimethyl-benzamide (56 mg, 21%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (250 mg, 0.50 mmol), methanesulfonyl chloride (47 µL, 0.60 mmol), triethylamine (84 µL, 0.60 mmol), zinc chloride (71 mg, 0.52 mmol), 4-chloro-N,N-dimethyl-2-methylamino-benzamide (110 mg, 0.52 mmol) and 4N NaOH (267 µL, 1.06 mmol).

MS ESI:524.9 [M+H]$^+$

EXAMPLE 31

Following General Procedure G, 4-chloro-2-{[4-(2,4-diamino-pyrimidin-5-ylmethyl)-6,7-dimethoxy-benzofuran-2-ylmethyl]-methyl-amino}-N-methyl-benzamide (52 mg, 17%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (300 mg, 0.60 mmol), methanesulfonyl chloride (56 µL, 0.72 mmol), triethylamine (100 µL, 0.72 mmol), zinc chloride (98 mg, 0.72 mmol), 4-chloro-N-methyl-2-methylamino-benzamide (143 mg, 0.72 mmol), and 4N NaOH (318 µL, 1.27 mmol).

MS ESI: 510.9 [M+H]$^+$

EXAMPLE 32

Following General Procedure G, 2-{[4-(2,4-diamino-pyrimidin-5-ylmethyl)-6,7-dimethoxy-benzofuran-2-ylmethyl]-methyl-amino}-4-fluoro-N,N-dimethyl-benzamide (40 mg, 16%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (250 mg, 0.50 mmol), methanesulfonyl chloride (47 µL, 0.60 mmol), triethylamine (84 µL, 0.60 mmol), zinc chloride (71 mg, 0.52 mmol), 4-chloro-N,N-dimethyl-2-methylamino-benzamide (102 mg, 0.52 mmol), and 4N NaOH (236 µL, 0.94 mmol).

MS ESI: 508.9 [M+H]$^+$

EXAMPLE 33

Following General Procedure G, 2-{[4-(2,4-diamino-pyrimidin-5-ylmethyl)-6,7-dimethoxy-benzofuran-2-ylmethyl]-amino}-5,N,N-trimethyl-benzamide (13 mg, 6.6%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (280 mg, 0.40 mmol), methanesulfonyl chloride (38 µL, 0.48 mmol), triethylamine (67 µL, 0.48 mmol), zinc chloride (64 mg, 0.47 mmol), 2-amino-5,N,N-trimethyl-benzamide (70 mg, 0.40 mmol), and 4N NaOH (641 µL, 2.56 mmol).

MS ESI: 490.9 [M+H]$^+$

EXAMPLE 34

Following General Procedure G, 2-{[4-(2,4-diamino-pyrimidin-5-ylmethyl)-6,7-dimethoxy-benzofuran-2-ylmethyl]-amino}-6-fluoro-N,N-dimethyl-benzamide (22 mg, 11%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (287 mg, 0.40 mmol), methanesulfonyl chloride (31 µL, 0.40 mmol), triethylamine (56 µL, 0.40 mmol), zinc chloride (66 mg, 0.40 mmol), 2-amino-6-fluoro-N,N-dimethyl-benzamide (74 mg, 0.40 mmol) and 4N NaOH (593 µL, 2.37 mmol).

MS ESI: 495.1 [M+H]$^+$

EXAMPLE 35

Following General Procedure G, 2-{[4-(2,4-diamino-pyrimidin-5-ylmethyl)-6,7-dimethoxy-benzofuran-2-ylmethyl]-amino}-N,N-dimethyl-benzamide (55 mg, 23%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (250 mg, 0.50 mmol), methanesulfonyl chloride (47 µL, 0.60 mmol), triethylamine (84 µL, 0.60 mmol), zinc chloride (82 mg, 0.60 mmol), 2-amino-N,N-dimethyl-benzamide (98 mg, 0.60 mmol), and 4N NaOH (340 L, 1.37 mmol).

MS ESI: 477.0 [M+H]$^+$

EXAMPLE 36

Following General Procedure G, 2-{[4-(2,4-Diamino-pyrimidin-5-ylmethyl)-6,7-dimethoxy-benzofuran-2-ylm-ethyl]-methyl-amino}-N,N-dimethyl-benzamide (68 mg, 23%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (300 mg, 0.60 mmol), methanesulfonyl chloride (60 µL, 0.72 mmol), triethylamine (100 µL, 0.72 mmol), zinc chloride (83 mg, 0.61 mmol), 2-amino-N,N-dimethyl-benzamide (109 mg, 0.61 mmol), and 4N NaOH (286 µL, 1.14 mmol).

MS ESI: 491.0 [M+H]$^+$

EXAMPLE 37

Following General Procedure G, 2-{[4-(2,4-diamino-pyrimidin-5-ylmethyl)-6,7-dimethoxy-benzofuran-2-ylmethyl]-amino}-3-methoxy-N,N-dimethyl-benzamide (25.8 mg, 13%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (280 mg, 0.40 mmol), methanesulfonyl chloride (37 µL, 0.48 mmol), triethylamine (67 µL, 0.48 mmol), zinc chloride (64 mg, 0.47 mmol), 2-amino-3-methoxy-N, N-dimethyl-benzamide (76 mg, 0.40 mmol), and 4N NaOH (666 µL, 1.92 mmol).

MS ESI: 507.1 [M+H]$^+$

General Procedure H: Oxidation of Alcohol into Aldehyde (Scheme 5)

Under argon and at room temperature, to a solution of compound X (1 eq.) in dichloromethane, manganese dioxide (10 eq.) was added at room temperature. The suspension was stirred under argon until completion. The resulting reaction mixture was filtered over celite, dried over MgSO$_4$ and the solvent evaporated under reduced pressure. The compound XVII was obtained after purification by FC, eluting with a gradient from cyclohexane to cyclohexane/EtOAc (1/2).

EXAMPLE 38

Following General Procedure H, N-[2-(2,2-dimethyl-propionylamino)-5-(2-formyl-6,7-dimethoxy-benzofuran-4-ylmethyl)-pyrimidin-4-yl]-2, 2-dimethyl-propionamide (650 mg, 27%) was obtained by reacting N-[2-(2,2-dimethyl-propionylamino)-5-(2-hydroxymethyl-6,7-dimethoxy-benzofuran-4-ylmethyl)-pyrimidin-4-yl]-2,2-dimethyl-propionamide (2.85 g, 5.73 mmol) and manganese dioxide (5.0 g, 57.37 mmol).

MS ESI: 497.1 [M+H]$^+$

EXAMPLE 39

Following General Procedure H, N-[5-(2-Formyl-6,7-dimethoxy-benzofuran-4-ylmethyl)-2-isobutyrylamino-pyrimidin-4-yl]-isobutyramide was obtained and used for the next step without further purification.

MS ESI: 469.0 [M+H]$^+$

General Procedure I: Reductive Amination with p-TosOH (Scheme 5)

Under argon and at room temperature, to a solution of compound XVII (1 eq.) and anthranilic acid derivative XI (1 eq.) in toluene was added p-toluenesulfonic acid (0.2 eq.). The resulting mixture was heated at 110° C. for 5 days. Sodium borohydride (2 eq.) was added and the mixture was stirred at room temperature.

After the reaction was completed, the mixture was quenched with water, extracted with dichloromethane, and the organic layer was washed with a saturated solution of NaHCO$_3$, brine. After drying over MgSO$_4$ and evaporation of the solvent under reduced pressure, compound XII was obtained. The compound XII (1 eq.) thus obtained was dissolved in methanol or isopropanol and an excess of a 4N NaOH solution (10 eq.) was added. The resulting mixture was heated at 50° C. until completion. The reaction was quenched with water and extracted with dichloromethane. The organic layer was washed with a saturated solution of NaHCO$_3$, water, brine, dried over MgSO$_4$, and evaporated under reduced pressure. Compound I was obtained after purification by FC, eluting with a gradient from CH$_2$Cl$_2$ to CH$_2$Cl$_2$/methanol (9/1).

EXAMPLE 40

Following General Procedure I, 4-chloro-2-{[4-(2,4-di-amino-pyrimidin-5-ylmethyl)-6,7-dimethoxy-benzofuran-2-ylmethyl]-amino}-N,N-dimethyl-benzamide (18 mg, 35%) was obtained by reacting N-[2-(2,2-dimethyl-propionylamino)-5-(2-formyl-6,7-dimethoxy-benzofuran-4-ylmethyl)-pyrimidin-4-yl]-2,2-dimethyl-propionamide (50 mg, 0.1 mmol), 2-amino-4-chloro-N,N-dimethyl-benzamide (20 mg, 0.1 mmol), p-toluenesulfonic acid (4 mg, 0.02 mmol), and sodium borohydride (8 mg, 0.2 mmol).

MS ESI: 510.1 [M+H]$^+$

General Procedure J: Reductive Amination with TFA (Scheme 6)

Under argon and at room temperature, to a solution of compound XVII (1 eq.) in THF freshly distilled, was added aniline XVIII (1 eq.) and trifluoroacetic acid (2 to 6 eq). The resulting mixture was stirred and heated at 50° C. for 3 hours. After cooling at −10° C., sodium triacetoxyborohydride (2 to 3 eq) was added. The reaction mixture was stirred at room temperature until completion. The mixture was diluted with ethyl acetate, and the organic layer was then washed with a saturated solution of NaHCO$_3$, dried over MgSO$_4$, and evaporated under reduced pressure. The intermediate obtained was used for the next step without further purification.

EXAMPLE 41

Following General Procedure J, the mixture XIX (see scheme 6) containing 2-{[4-(2,4-bis-isobutyrylamino-pyrimidin-5-ylmethyl)-6,7-dimethoxy-benzofuran-2-ylmethyl]-amino}-4-chloro-benzoic acid and 2-{[4-(2-amino-4-isobutyrylamino-pyrimidin-5-ylmethyl)-6,7-dimethoxy-benzofuran-2-ylmethyl]-amino}-4-chloro-benzoic acid (ratio 1:2) (quantitative yield from HPLC-MS profile) was obtained by reacting N-[5-(2-Formyl-6,7-dimethoxy-benzofuran-4-ylmethyl)-2-isobutyrylamino-pyrimidin-4-yl]-isobutyramide (1 g, 2.13 mmol), 2-amino-4-chloro-benzoic acid (366 mg, 2.13 mmol), trifluoroacetic acid (327 µL, 4.27 mmol), and sodium triacetoxyborohydride (1.35 g, 6.40 mmol). This mixture was used without further purification in the general procedure O.

MS ESI: 624.3 [M+H]$^+$
MS ESI: 554.2 [M+H]$^+$

EXAMPLE 42

Following General Procedure J, 2-{[4-(2-amino-4-isobutyrylamino-pyrimidin-5-ylmethyl)-6,7-dimethoxy-benzofuran-2-ylmethyl]-amino}-4-chloro-N-isopropyl-N-methyl-benzamide (3.6 g, 55%) was obtained by reacting N-[5-(2-Formyl-6,7-dimethoxy-benzofuran-4-ylmethyl)-2-isobutyrylamino-pyrimidin-4-yl]-isobutyramide (5 g, 10.68 mmol), 2-amino-4-chloro-N-isopropyl-N-methyl-benzamide (2.4 g, 10.68 mmol), trifluoroacetic acid (2.45 mL, 32.04 mmol), sodium triacetoxyborohydride (6.79 g, 32.04 mmol).

MS ESI: 609.0 [M+H]$^+$

EXAMPLE 43

Following General Procedure J, N-(4-Amino-5-{2-[(5-chloro-2-cyano-phenylamino]-methyl}-6,7-dimethoxy-benzofuran-4-ylmethyl)-pyrimidin-2-yl)-isobutyramide (quantitative yield from HPLC-MS profile) was obtained by reacting N-[5-(2-formyl-6,7-dimethoxy-benzofuran-4-ylmethyl)-2-isobutyrylamino-pyrimidin-4-yl]-isobutyramide (100 mg, 0.21 mmol), 2-amino-4-chloro-benzonitrile (33 mg, 0.21 mmol), trifluoroacetic acid (33 µL, 0.42 mmol), sodium triacetoxyborohydride (90 mg, 0.42 mmol).

MS ESI: 535 [M+H]$^+$

EXAMPLE 44

Following General Procedure J, N-[4-amino-5-(2-{[5-chloro-2-(morpholine-4-carbonyl)-phenylamino]-methyl}-6,7-dimethoxy-benzofuran-4-ylmethyl)-pyrimidin-2-yl]-isobutyramide (quantitative yield from HPLC-MS profile) was obtained by reacting N-[5-(2-formyl-6,7-dimethoxy-benzofuran-4-ylmethyl)-4-isobutyrylamino-pyrimidin-2-yl]-isobutyramide (100 mg, 0.21 mmol), (2-amino-4-chloro-phenyl)-morpholin-4-yl-methanone (51 mg, 0.21 mmol), trifluoroacetic acid (98 µL, 1.28 mmol), sodium triacetoxyborohydride (135 mg, 0.64 mmol).

MS ESI: 623.0 [M+H]$^+$

General Procedure K: Deprotection of Diaminopyrimidine (Scheme 6)

The compound (1 eq.) obtained following the general procedure J was dissolved in methanol or isopropanol and an excess of a 4N NaOH solution (4 to 10 eq.) was added. The resulting mixture was heated at 50° C. After completion, the reaction was quenched with water and extracted with dichloromethane. The organic layer was washed with a saturated solution of NaHCO$_3$, water, brine, dried over MgSO$_4$, and evaporated under reduced pressure. The compound I was obtained after purification by FC, eluting with a gradient from CH$_2$Cl$_2$ to CH$_2$Cl2/methanol (9/1).

EXAMPLE 45

Following General Procedure K, 4-chloro-2-{[4-(2,4-di-amino-pyrimidin-5-ylmethyl)-6,7-dimethoxy-benzofuran-2-ylmethyl]-amino}-benzoic acid (10 mg, 13%) was obtained by reacting the mixture XIX (see scheme 6) containing 2-{[4-(2,4-Bis-isobutyrylamino-pyrimidin-5-ylmethyl)-6,7-dimethoxy-benzofuran-2-ylmethyl]-amino}-4-chloro-benzoic acid and 2-{[4-(2-Amino-4-isobutyrylamino-pyrimidin-5-ylmethyl)-6,7-dimethoxy-benzofuran-2-ylmethyl]-amino}-4-chloro-benzoic acid (ratio 1:2) described in the general procedure J (100 mg, 0.16 mmol) and 4 N NaOH (400 µL, 1.6 mmol).

MS ESI: 484.3 [M+H]$^+$

EXAMPLE 46

Following General Procedure K, 4-chloro-2-{[4-(2,4-di-amino-pyrimidin-5-ylmethyl)-6,7-dimethoxy-benzofuran-2-ylmethyl]-amino}-N-isopropyl-N-methyl-benzamide (908 mg, 28.5%) was obtained by reacting 2-{[4-(2-amino-4-isobutyrylamino-pyrimidin-5-ylmethyl)-6,7-dimethoxy-benzofuran-2-ylmethyl]-amino}-4-chloro-N-isopropyl-N-methyl-benzamide (3.6 g, 5.9 mmol) and 4N NaOH (5.34 mL, 21.36 mmol)

MS ESI: 539.0 [M+H]$^+$

EXAMPLE 47

Following General Procedure K, 4-chloro-2-{[4-(2,4-di-amino-pyrimidin-5-ylmethyl)-6,7-dimethoxy-benzofuran-2-ylmethyl]-amino}-benzonitrile (24 mg, 25%) was obtained by reacting N-(4-amino-5-{2-[(5-chloro-2-cyano-phenylamino)-methyl]-6,7-dimethoxy-benzofuran-4-ylmethyl}-pyrimidin-2-yl)-isobutyramide (128 mg, 0.21 mmol) and 4N NaOH (213 µL, 0.85 mmol)

MS ESI: 465.0 [M+H]$^+$

EXAMPLE 48

Following General Procedure K, (4-chloro-2-{[4-(2,4-di-amino-pyrimidin-5-ylmethyl)-6,7-dimethoxy-benzofuran-2-ylmethyl]-amino}-phenyl)-morpholin-4-yl-methanone (47 mg, 25%) was obtained by reacting N-[4-Amino-5-(2-{[5-chloro-2-(morpholine-4-carbonyl)-phenylamino]-methyl}-6,7-dimethoxy-benzofuran-4-ylmethyl)-pyrimidin-2-yl]-isobutyramide (213 mg, 0.34 mmol) and 4N NaOH (342 µL, 1.37 mmol)

MS ESI: 553.1 [M+H]$^+$

General Procedure L: Amide Formation and Deprotection (Scheme 6)

Under argon and at room temperature, to a suspension in dichloromethane of the mixture XIX previously described in the general procedure J (1 eq.), 1-hydroxybenzotriazole hydrate (1.2 eq.), (3-dimethylamino-propyl)-ethyl-carbodiimide hydrochloride (1.2 eq.) and the amine XIV (1.2 eq.) were added. The resulting mixture was stirred at 40° C. until completion. The mixture was diluted with dichloromethane, washed with a saturated solution of NaHCO$_3$ and brine. After drying over MgSO$_4$ and evaporation of the solvent under reduced pressure, compound was obtained.

The compound (1 eq.) so obtained was dissolved in methanol or isopropanol and an excess of a 4N NaOH solution (6 eq.) was added. The resulting mixture was heated at 50° C. overnight or 10 minutes at 110° C. in the microwave. The reaction was quenched with water and extracted with dichloromethane. The organic layer was washed with a saturated solution of NaHCO$_3$, water, brine, dried over MgSO$_4$, and evaporated under reduced pressure. The compound I was obtained after purification by FC, eluting with a gradient from CH$_2$Cl$_2$ to CH$_2$Cl$_2$/methanol (9/1).

EXAMPLE 49

Following General Procedure L, 4-chloro-2-{[4-(2,4-di-amino-pyrimidin-5-ylmethyl)-6,7-dimethoxy-benzofuran-2-ylmethyl]-amino}-N-isopropyl-N-methyl-benzamide (18 mg, 9%) was obtained by reacting mixture XIX (see scheme 6) containing 2-{[4-(2,4-bis-isobutyrylamino-pyrimidin-5-ylmethyl)-6,7-dimethoxy-benzofuran-2-ylmethyl]-amino}-4-chloro-benzoic acid and 2-{[4-(2-amino-4-isobutyrylamino-pyrimidin-5-ylmethyl)-6,7-dimethoxy-benzofuran-2-ylmethyl]-amino}-4-chloro-benzoic acid (ratio 1:2) (200 mg, 0.32 mmol), 1-hydroxybenzotriazole hydrate (52 mg, 0.38 mmol), (3-dimethylamino-propyl)-ethyl-carbodiimide hydrochloride (74 mg, 0.38 mmol), N-isopropylmethylamine (28 mg, 0.38 mmol) and 4N NaOH (480 µL, 1.92 mmol).

MS ESI: 539.3 [M+H]$^+$

EXAMPLE 50

Following General Procedure L, N-butyl-4-chloro-2-{[4-(2,4-diamino-pyrimidin-5-ylmethyl)-6,7-dimethoxy-benzofuran-2-ylmethyl]-amino}-N-methyl-benzamide (16 mg, 9%) was obtained by reacting mixture XIX (see scheme 6) containing 2-{[4-(2,4-bis-isobutyrylamino-pyrimidin-5-ylmethyl)-6,7-dimethoxy-benzofuran-2-ylmethyl]-amino}-4-chloro-benzoic acid and 2-{[4-(2-amino-4-isobutyrylamino-pyrimidin-5-ylmethyl)-6,7-dimethoxy-benzofuran-2-ylmethyl]-amino}-4-chloro-benzoic acid (ratio 1:2) (200 mg, 0.32 mmol), 1-hydroxybenzotriazole hydrate (52 mg, 0.38 mmol), (3-dimethylamino-propyl)-ethyl-carbodiimide hydrochloride (74 mg, 0.38 mmol), N-butylmethylamine (34 mg, 0.38 mmol) and 4N NaOH (480 µL, 1.92 mmol).

MS ESI: 553.3 [M+H]$^+$

EXAMPLE 51

Following General Procedure L, 4-Chloro-2-{[4-(2,4-di-amino-pyrimidin-5-ylmethyl)-6,7-dimethoxy-benzofuran-2-ylmethyl]-amino}-N-(2-dimethylamino-ethyl)-N-methyl-benzamide (15 mg, 8%) was obtained by reacting mixture XIX (see scheme 6) containing 2-{[4-(2,4-Bis-isobutyrylamino-pyrimidin-5-ylmethyl)-6,7-dimethoxy-benzofuran-2-ylmethyl]-amino}-4-chloro-benzoic acid and 2-{[4-(2-Amino-4-isobutyrylamino-pyrimidin-5-ylmethyl)-6,7-dimethoxy-benzofuran-2-ylmethyl]-amino}-4-chloro-benzoic acid (ratio 1:2) (200 mg, 0.32 mmol), 1-hydroxybenzotriazole hydrate (52 mg, 0.38 mmol), (3-dimethylamino-propyl)-ethyl-carbodiimide hydrochloride (74 mg, 0.38 mmol), N-N-N'-trimethylendiamine (39 mg, 0.38 mmol) and 4N NaOH (480 µL, 1.92 mmol).

MS ESI: 568.3 [M+H]$^+$

EXAMPLE 52

Following General Procedure L, (4-chloro-2-{[4-(2,4-di-amino-pyrimidin-5-ylmethyl)-6,7-dimethoxy-benzofuran-2-ylmethyl]-amino}-phenyl)-[4-(2-dimethylamino-ethyl)-piperazin-1-yl]-methanone (10 mg, 5%) was obtained by reacting mixture XIX (see scheme 6) containing 2-{[4-(2,4-bis-isobutyrylamino-pyrimidin-5-ylmethyl)-6,7-dimethoxy-benzofuran-2-ylmethyl]-amino}-4-chloro-benzoic acid and 2-{[4-(2-amino-4-isobutyrylamino-pyrimidin-5-ylmethyl)-6,7-dimethoxy-benzofuran-2-ylmethyl]-amino}-4-chloro-benzoic acid (ratio 1:2) (200 mg, 0.32 mmol), 1-hydroxybenzotriazole hydrate (52 mg, 0.38 mmol), (3-dimethylamino-propyl)-ethyl-carbodiimide hydrochloride (74 mg, 0.38 mmol), Dimethyl-(2-piperazin-1-yl-ethyl)-amine (60 mg, 0.38 mmol) and NaOH 4N (480 µL, 1.92 mmol).

MS ESI: 623.4 [M+H]$^+$

EXAMPLE 53

Following General Procedure L, 4-chloro-2-{[4-(2,4-di-amino-pyrimidin-5-ylmethyl)-6,7-dimethoxy-benzofuran-2-ylmethyl]-amino}-phenyl)-[4-(2-methoxy-ethyl)-piperazin-1-yl]-methanone (18 mg, 9%) was obtained by reacting mixture XIX (see scheme 6) containing 2-{[4-(2,4-bis-isobutyrylamino-pyrimidin-5-ylmethyl)-6,7-dimethoxy-benzofuran-2-ylmethyl]-amino}-4-chloro-benzoic acid and 2-{[4-(2-amino-4-isobutyrylamino-pyrimidin-5-ylmethyl)-6,7-dimethoxy-benzofuran-2-ylmethyl]-amino}-4-chloro-benzoic acid (ratio 1:2) (200 mg, 0.32 mmol), 1-hydroxybenzotriazole hydrate (52 mg, 0.38 mmol), (3-dimethylamino-propyl)-ethyl-carbodiimide hydrochloride (74 mg, 0.38 mmol), 1-(2-methoxy-ethyl)-piperazine (55 mg, 0.38 mmol) and 4N NaOH (480 µL, 1.92 mmol).

MS ESI: 610.6 [M+H]$^+$

Procedure M: Reductive Amination with Triethylorthoformate

Under argon and at room temperature, to a solution of compound XVII (1 eq.) in isopropanol, triethylorthoformate (2.8 eq.) and the anthranilic acid derivative XI (1 eq.) were added. The resulting mixture was stirred at 50° C. overnight. Sodium borohydride (4 eq.) was then added at room temperature. The mixture was then stirred at 50° C. until completion. The mixture was diluted with dichloromethane, washed with a saturated solution of NaHCO$_3$ and brine. After drying over MgSO$_4$ and evaporation of the solvent under reduced pressure, the compound (1 eq.) so obtained was dissolved in methanol or isopropanol and an excess of a 4N NaOH solution (6 eq.) was added. The resulting mixture was heated at 50° C. until completion. The reaction was quenched with water and extracted with dichloromethane. The organic layer was washed with a saturated solution of NaHCO$_3$, water, brine, dried over MgSO$_4$, and evaporated under reduced pressure. The compound was obtained after purification by FC, eluting with a gradient from CH$_2$Cl$_2$ to CH$_2$Cl$_2$/methanol (9/1).

EXAMPLE 54

Following General Procedure M, N-carbamoylmethyl-4-chloro-2-{[4-(2,4-diamino-pyrimidin-5-ylmethyl)-6,7-dimethoxy-benzofuran-2-ylmethyl]-amino}-N-methyl-benzamide (7 mg, 3%) was obtained by reacting N-[5-(2-formyl-6,7-dimethoxy-benzofuran-4-ylmethyl)-2-isobutyrylamino-pyrimidin-4-yl]-isobutyramide (200 mg, 0.43 mmol), 2-amino-N-carbamoylmethyl-4-chloro-N-methyl-benzamide (103 mg, 0.43 mmol), triethylorthoformate (130 µL, 1.19 mmol) and NaBH$_4$ (64 mg, 1.71 mmol)

MS ESI: 554.1 [M+H]$^+$

General Procedure N: Coupling Procedure with Anthranilic Acid Derivatives (Scheme 7)

Under argon and at room temperature, to a solution of the anthranilic acid derivative XI (1.1 eq.) in acetonitrile, compound XX (1 eq.) and triethylamine (1.1 eq.) were added stepwise. The resulting mixture was heated at 80° C. until completion. Ethyl acetate was added to the mixture and the organic layer was washed with water, a saturated solution of NaHCO$_3$ and brine. After drying over MgSO$_4$ and evaporation of the solvent under reduced pressure, compound I was purified by FC, eluting with a gradient from CH$_2$Cl$_2$ to CH$_2$Cl$_2$/methanol (93/7).

EXAMPLE 55

Following General Procedure N, 2-{[4-(2,4-diamino-pyrimidin-5-ylmethyl)-6,7-dimethoxy-benzofuran-2-ylmethyl]-amino}-4-fluoro-N,N-dimethyl-benzamide (20 mg, 3.5%) was obtained by reacting 5-(2-chloromethyl-6,7-dimethoxy-benzofuran-4-ylmethyl)-pyrimidine-2,4-diamine hydrochloride (443 mg, 1.15 mmol), 2-amino-4-fluoro-N,N-dimethyl-benzamide (230 mg, 1.26 mmol), and triethylamine (175 µL, 1.26 mmol).

MS ESI: 495.0 [M+H]$^+$

EXAMPLE 56

Following General Procedure N, 3-chloro-2-{[4-(2,4-diamino-pyrimidin-5-ylmethyl)-6,7-dimethoxy-benzofuran-2-ylmethyl]-amino}-N,N-dimethyl-benzamide (20 mg, 2.5%) was obtained by reacting 5-(2-chloromethyl-6,7-dimethoxy-benzofuran-4-ylmethyl)-pyrimidine-2,4-diamine hydrochloride (662 mg, 1.71 mmol), 2-amino-3-chloro-N,N-dimethyl-benzamide (375 mg, 1.89 mmol), and triethylamine (263 µL, 1.89 mmol)

MS ESI: 511.2 [M+H]$^+$

EXAMPLE 57

Following General Procedure N, 3,6-dichloro-2-{[4-(2,4-diamino-pyrimidin-5-ylmethyl)-6,7-dimethoxy-benzofuran-2-ylmethyl]-amino}-N,N-dimethyl-benzamide (19.2 mg, 2%) was obtained by reacting 5-(2-chloromethyl-6,7-dimethoxy-benzofuran-4-ylmethyl)-pyrimidine-2,4-diamine hydrochloride (665 mg, 1.72 mmol), 2-amino-3,5-dichloro-N,N-dimethyl-benzamide (440 mg, 1.89 mmol), and triethylamine (263 µL, 1.89 mmol).

MS ESI: 544.9 [M+H]$^{30}$

General Procedure O: Coupling with Phenol (Scheme 7)

Under argon and at room temperature, to a solution of phenol XXI (1.5 eq.) in DMF, sodium hydride 60% in oil (1.5 eq.) was added. After stirring for 30 minutes, a solution of compound XX in DMF was added. The resulting mixture was stirred at room temperature until completion of the reaction. The excess of solvent was evaporated under reduced pressure and the residue thus obtained was dissolved in dichloromethane, and washed with a saturated solution of NaHCO$_3$ and brine. After drying over MgSO$_4$ and evaporation of the solvent under reduced pressure, compound I was purified by FC, eluting with a gradient from CH$_2$Cl$_2$ to CH$_2$Cl$_2$/methanol (9/1).

EXAMPLE 58

Following General Procedure O, 3,5-dichloro-2-[4-(2,4-diamino-pyrimidin-5-ylmethyl)-6,7-dimethoxy-benzofuran-2-ylmethoxy]-N,N-dimethyl-benzamide (98 mg, 15%) was obtained by reacting 5-(2-chloromethyl-6,7-dimethoxy-benzofuran-4-ylmethyl)-pyrimidine-2,4-diamine hydrochloride (450 mg, 1.16 mmol), 3,5-dichloro-2-hydroxy-N,N-dimethyl-benzamide (410 mg, 1.75 mmol), and sodium hydride (70 mg, 1.75 mmol).

MS ESI: 547.2 [M+H]$^+$

EXAMPLE 59

Following General Procedure O, 4-chloro-2-[4-(2,4-diamino-pyrimidin-5-ylmethyl)-6,7-dimethoxy-benzofuran-2-ylmethoxy]-N-methyl-benzamide (36 mg, 10%) was obtained by reacting 5-(2-chloromethyl-6,7-dimethoxy-benzofuran-4-ylmethyl)-pyrimidine-2,4-diamine hydrochloride (280 mg, 0.72 mmol), 4-chloro-2-hydroxy-N-methyl-benzamide (201 mg, 1.09 mmol) and sodium hydride (44 mg, 1.09 mmol).

MS ESI: 498.0 [M+H]$^+$

EXAMPLE 60

Following General Procedure O, 2-[4-(2,4-Diamino-pyrimidin-5-ylmethyl)-6,7-dimethoxy-benzofuran-2-ylmethoxy]-5-fluoro-N,N-dimethyl-benzamide (44 mg, 7%) was obtained by reacting 5-(2-chloromethyl-6,7-dimethoxy-benzofuran-4-ylmethyl)-pyrimidine-2,4-diamine hydrochloride (480 mg, 1.24 mmol), 5-Fluoro-2-hydroxy-N,N-dimethyl-benzamide (342 mg, 1.87 mmol), and sodium hydride (75 mg, 1.87 mmol).

MS ESI: 496.2 [M+H]$^+$

EXAMPLE 61

Following General Procedure 0, 4-chloro-2-[4-(2,4-diamino-pyrimidin-5-ylmethyl)-6,7-dimethoxy-benzofuran- 2-ylmethoxy]-N,N-dimethyl-benzamide (1.3 mg, 3.5%) was obtained by reacting 5-(2-chloromethyl-6,7-dimethoxy-benzofuran-4-ylmethyl)-pyrimidine-2,4-diamine hydrochloride (280 mg, 0.72 mmol), 4-chloro-2-hydroxy-N,N-dimethyl-benzamide (217 mg, 1.09 mmol) and sodium hydride (44 mg, 1.09 mmol).

MS ESI: 512.1 [M+H]+

General Procedure P: Measurement of Antimicrobial Activity

Antimicrobial susceptibility testing was performed in accordance with the National Committee for Clinical Laboratory Standards (NCCLS) procedure [M7-A5, 2001]. M7-A5 (2001): Methods for Dilution Antimicrobial Susceptibility Tests for Bacteria That Grow Aerobically; Approved Standard —Fifth Edition American National Standard General Procedure Q: Purified Enzymes and DHFR Enzyme Assay:

Bacterial and human dihydrofolate reductases were purified, shown to be functional and used in DHFR assays as described by Baccanari & Joyner (Baccanari, D. P. and Joyner, S. S. 1981. Dihdrofolate reductase hysteresis and its effect on inhibitor binding analyses. Biochem. 20, 1710-1716)

What is claimed is:
1. A compound of Formula I,

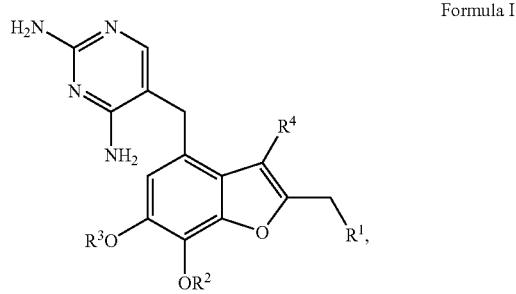

Formula I wherein
$R^1$ represents

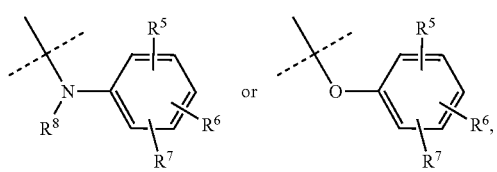

wherein $R^5$ is cyano, carboxylic acid or the group

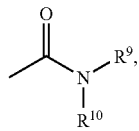

wherein
$R^9$ represents hydrogen, lower alkyloxy, lower alkylamino, lower alkyl with 1 to 6 carbon atoms, aminocarbonylalkyl, mono- or dialkylaminoalkyl, alkyloxyalkyl, arylalkyl, aryl, or heteroaryl, wherein the aryl and heteroaryl groups can be optionally mono-, di-, or tri-substituted with straight or branched chain lower alkyl with 1 to 4 carbon atoms, wherein these substituents may be the same or different;

$R^{10}$ represents hydrogen, or lower alkyl with 1 to 4 carbon atoms; or $R^9$ and $R^{10}$ together with the nitrogen atom to which they are attached, form a 3-, 4-, 5- or 6- membered heterocyclic ring, wherein the 5- or 6-membered ring optionally contains an additional heteroatom selected from the group consisting of oxygen, nitrogen and sulfur, wherein, if the additional heteroatom is nitrogen, the additional nitrogen can be substituted with lower alkyl with 1 to 4 carbon atoms, mono- or dialkylaminoalkyl or alkyloxyalkyl;

$R^6$ represents hydrogen, halogen, straight or branched chain lower alkyl with 1 to 4 carbon atoms, or lower alkyloxy;

$R^7$ represents hydrogen or halogen; and $R^8$ represents hydrogen or straight or branched chain lower alkyl with 1 to 4 carbon atoms;

$R^2$ and $R^3$ independently represent hydrogen, lower alkyl with 1 to 3 carbon atoms; or together a lower alkylene group with 1 to 3 carbon atoms bridging the oxygen atoms and forming a five, six or seven membered ring; and $R^4$ represents hydrogen or lower alkyl with 1 to 4 carbon atoms, or a pharmaceutically acceptable salt thereof.

2. The compound of claim 1, represented by Formula II,

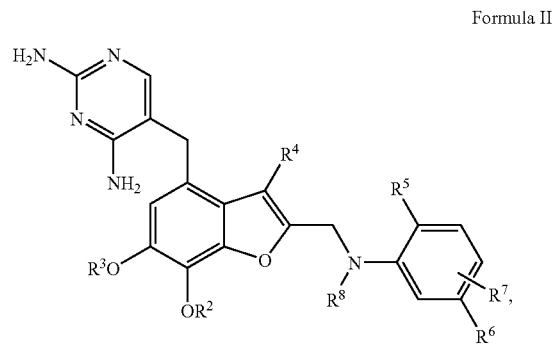

Formula II wherein
$R^2$ and $R^3$ represent methyl; and
$R^4$ represents hydrogen.

3. The compound of claim 1, represented by Formula III,

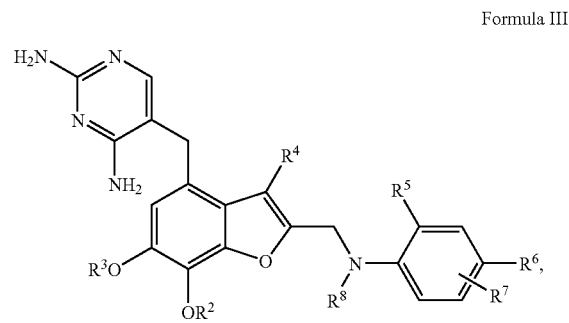

Formula III wherein
$R^2$ and $R^3$ represent methyl; and
$R^4$ represents hydrogen.

4. The compound of claim 1, represented by Formula IV,

Formula IV

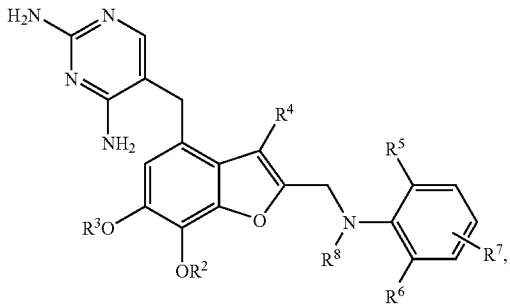

wherein
R² and R³ represent methyl; and
R⁴ represents hydrogen.

5. The compound of claim 1, represented by Formula V,

Formula V

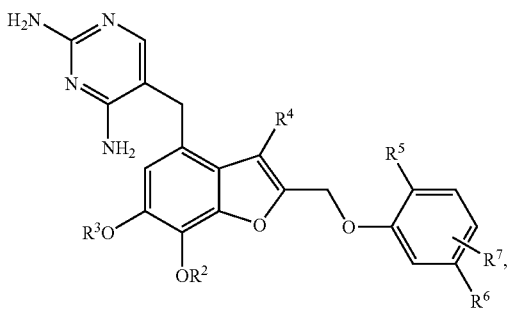

wherein
R² and R³ represent methyl; and
R⁴ represents hydrogen.

6. The compound of claim 1, represented by Formula VI,

Formula VI

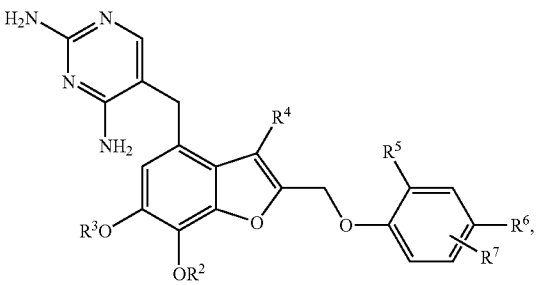

wherein
R² and R³ represent methyl; and
R⁴ represents hydrogen.

7. The compound of claim 1,
wherein
R⁵ is carboxylic acid dimethylamide, carboxylic acid methylamide, carboxylic acid diethylamide, carboxylic acid methoxyethylamine, pyrrolidin-1-yl-methanone, morpholin-4-yl-methanone, carboxylic acid methylamide, piperidin-1-yl-methanone; carboxylic acid N-(1, 3,5-trimethyl-1H-pyrazol-4-yl)-amide, carboxylic acid N-methyl-benzyl-amide 4-(2-methoxy-ethyl)-piperazin1-yl-methanone, 4-(2-dimethylamino-ethyl)-piperazin1-yl-methanone, carboxylic acid N-(2-dimethylamino-ethyl)-N-methyl-amide, carboxylic acid N-butyl- N-methyl-amide, carboxylic acid N-isopropyl-N-methyl-amide, carboxylic acid N-carbamoylmethyl-N-methyl-amide, carboxylic acid, or cyano;
R⁶ represents hydrogen, fluoro, chloro or methoxy;
R⁷ represents hydrogen, fluoro or chloro; and
R⁸ represents hydrogen or methyl.

8. A compound selected from the group consisting of:
(4-Chloro-2-{[4-(2,4-diamino-pyrimidin-5-ylmethyl)-6, 7-dimethoxy-benzofuran-2-ylmethyl]-amino}-phenyl)-pyrrolidin-1-yl-methanone;

4-Chloro-2-{[4-(2,4-diamino-pyrimidin-5-ylmethyl)-6,7-dimethoxy-benzofuran-2-ylmethyl]-amino}N,N-diethyl-benzamide;

(4-Chloro-2-{[4-(2,4-diamino-pyrimidin-5-ylmethyl)-6, 7-dimethoxy-benzofuran-2-ylmethyl]-amino}phenyl)-piperidin-1-yl-methanone;

4-Chloro-2-{[4-(2,4-diamino-pyrimidin-5-ylmethyl)-6,7-dimethoxy-benzofuran-2-ylmethyl]-amino}-N-(1,3,5-trimethyl-1H-pyrazol-4-yl)-benzamide;

N-Benzyl-4-chloro-2-{[4-(2,4-diamino-pyrimidin-5-ylmethyl)-6,7-dimethoxy-benzofuran -2-ylmethyl]-amino}-N -methyl-benzamide;

4-Chloro-2-{[4-(2,4-diamino-pyrimidin-5-ylmethyl)-6,7-dimethoxy-benzofuran-2-ylmethyl]-amino}-N,N-dimethyl-benzamide;

5-Chloro-2-{[4-(2,4-diamino-pyrimidin-5-ylmethyl)-6,7-dimethoxy-benzofuran-2-ylmethyl]-amino}-N,N-dimethyl-benzamide;

4-Chloro-2-{[4-(2,4-diamino-pyrimidin-5-ylmethyl)-6,7-dimethoxy-benzofuran-2-ylmethyl]-methyl-amino}-N, N-dimethyl-benzamide;

4-Chloro-2-{[4-(2,4-diamino-pyrimidin-5-ylmethyl)-6,7-dimethoxy-benzofuran-2-ylmethyl]-methyl-amino}-N-methyl-benzamide;

2-{[4-(2,4-Diamino-pyrimidin-5-ylmethyl)-6,7-dimethoxy-benzofuran-2-ylmethyl]-methyl-amino}-4-fluoro-N,N-dimethyl-benzamide;

2-{[4-(2,4-Diamino-pyrimidin-5-ylmethyl)-6,7-dimethoxy-benzofuran-2-ylmethyl]-amino}-5,N,N-trimethyl-benzamide;

2-{[4-(2,4-Diamino-pyrimidin-5-ylmethyl)-6,7-dimethoxy-benzofuran-2-ylmethyl]-amino}-6-fluoro-N,N-dimethyl-benzamide;

2-{[4-(2,4-Diamino-pyrimidin-5-ylmethyl)-6,7-dimethoxy-benzofuran-2-ylmethyl]-amino}-N,N-dimethyl-benzamide;

2-{[4-(2,4-Diamino-pyrimidin-5-ylmethyl)-6,7-dimethoxy-benzofuran-2-ylmethyl]-amino}-4-fluoro-N,N-dimethyl-benzamide;

3-Chloro-2-{[4-(2,4-diamino-pyrimidin-5-ylmethyl)-6,7-dimethoxy-benzofuran-2-ylmethyl]-amino}-N,N-dimethyl-benzamide;

3,5-Dichloro-2-[4-(2,4-diamino-pyrimidin-5-ylmethyl)-6,7-dimethoxy-benzofuran-2-ylmethoxy]-N,N-dimethyl-benzamide;

4-Chloro-2-[4-(2,4-diamino-pyrimidin-5-ylmethyl)-6,7-dimethoxy-benzofuran-2-ylmethoxy]-N-methyl-benzamide;

2-[4-(2,4-Diamino-pyrimidin-5-ylmethyl)-6,7-dimethoxy-benzofuran-2-ylmethoxy]-5-fluoro-N,N-dimethyl-benzamide;

2-{[4-(2,4-Diamino-pyrimidin-5-ylmethyl)-6,7-dimethoxy-benzofuran-2-ylmethyl]-amino}-3-methoxy-N,N-dimethyl-benzamide;
2-{[4-(2,4-Diamino-pyrimidin-5-ylmethyl)-6,7-dimethoxy-benzofuran-2-ylmethyl]-methyl-amino}-N,N-dimethyl-benzamide;
3,6-Dichloro-2-{[4-(2,4-diamino-pyrimidin-5-ylmethyl)-6,7-dimethoxy-benzofuran-2-ylmethyl]-amino}-N,N-dimethyl-benzamide;
4-Chloro-2-[4-(2,4-diamino-pyrimidin-5-ylmethyl)-6,7-dimethoxy-benzofuran-2-ylmethoxy]-N,N-dimethyl-benzamide;
(4-Chloro-2-{[4-(2,4-diamino-pyrimidin-5-ylmethyl)-6,7-dimethoxy-benzofuran-2-ylmethyl]-amino}-phenyl)-morpholin-4-yl-methanone;
(4-Chloro-2-{[4-(2,4-diamino-pyrimidin-5-ylmethyl)-6,7-dimethoxy-benzofuran-2-ylmethyl]-amino}-benzonitrile;
4-Chloro-2-{[4-(2,4-diamino-pyrimidin-5-ylmethyl)-6,7-dimethoxy-benzofuran-2-ylmethyl]-amino}-N-isopropyl-N-methyl-benzamide;
N-Butyl-4-chloro-2-{[4-(2,4-diamino-pyrimidin-5-ylmethyl)-6,7-dimethoxy-benzofuran-2-ylmethyl]-amino}-N-methyl-benzamide;
4-Chloro-2-{[4-(2,4-diamino-pyrimidin-5-ylmethyl)-6,7-dimethoxy-benzofuran-2-ylmethyl]amino}-benzoic acid;
4-Chloro-2-{[4-(2,4-diamino-pyrimidin-5-ylmethyl)-6,7-dimethoxy-benzofuran-2-ylmethyl]-amino}-N-(2-dimethylamino-ethyl)-N-methyl-benzamide;
4-Chloro-2-{[4-(2,4-diamino-pyrimidin-5-ylmethyl)-6,7-dimethoxy-benzofuran-2-ylmethyl]-amino}-phenyl)-[4-(2-dimethylamino-ethyl)-piperazin-1-yl]-methanone;
(4-Chloro-2-{[4-(2,4-diamino-pyrimidin-5-ylmethyl)-6,7-dimethoxy-benzofuran-2-ylmethyl]-amino}-phenyl)-[4-(2-methoxy-ethyl)-piperazin-1-yl]-methanone; and
N-Carbamoylmethyl-4-chloro-2-{[4-(2,4-diamino-pyrimidin-5-ylmethyl)-6,7-dimethoxy-benzofuran-2-ylmethyl]amino}-N-methyl-benzamide,
or a pharmaceutically acceptable salt thereof.

9. A compound represented by formula X, XVI or XVII,

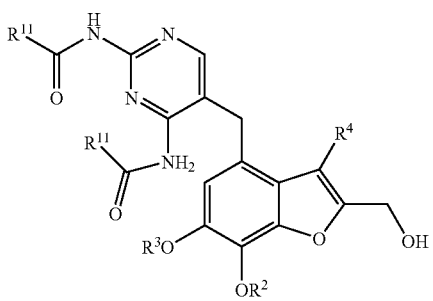

X

-continued

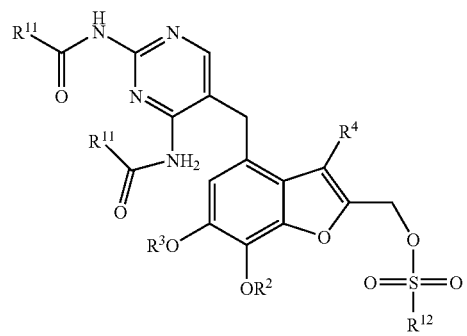

XVI

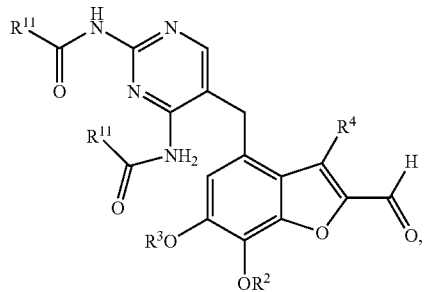

XVII wherein $R^2$ and $R^3$ independently represent hydrogen, lower alkyl with 1 to 3 carbon atoms; or together a lower alkylene group with 1 to 3 carbon atoms bridging the oxygen atoms and forming a five, six or seven membered ring;

$R^4$ represents hydrogen or lower alkyl with 1 to 4 carbon atoms;

$R^{11}$ represents straight or branched chain lower alkyl; and $R^{12}$ represents lower alkyl or aryl.

10. A pharmaceutical composition comprising one or more compounds of any one of claims 1 to 8 and an inert carrier.

11. A process for the manufacture of a pharmaceutical composition comprising one or more compounds as claimed in any one of claims 1 to 8 as an active ingredient, which process comprises mixing one or more active ingredients with a pharmaceutically acceptable med carrier or an adjuvant, or both.

12. A method for treating a bacterial infection caused by a bacterium that can be inhibited through inhibition of its dihydrofolate reductase enzyme comprising administering to a subject in need thereof the pharmaceutical composition of claim 10.

13. The method of claim 12, wherein said bacterial infection is caused by a Gram positive or Gram negative pathogen, or by a mixture thereof.

* * * * *